US010654941B2

United States Patent
Wilmen et al.

(10) Patent No.: US 10,654,941 B2
(45) Date of Patent: May 19, 2020

(54) ANTIBODIES AGAINST FACTOR XI AND USES THEREOF

(71) Applicants: Bayer Pharma Aktiengesellschaft, Berlin (DE); ARONORA INC., Portland, OR (US)

(72) Inventors: Andreas Wilmen, Köln (DE); Anja Buchmüller, Essen (DE); Erik Tucker, Portland, OR (US)

(73) Assignees: Bayer Pharma Aktiengesellschaft, Berlin (DE); ARONORA INC., Portland, OR (US)

( * ) Notice: Subject to any disclaimer, the term of this patent is extended or adjusted under 35 U.S.C. 154(b) by 0 days.

(21) Appl. No.: 16/335,133

(22) PCT Filed: Sep. 18, 2017

(86) PCT No.: PCT/EP2017/073410
§ 371 (c)(1),
(2) Date: Mar. 20, 2019

(87) PCT Pub. No.: WO2018/054813
PCT Pub. Date: Mar. 29, 2018

(65) Prior Publication Data
US 2019/0225705 A1    Jul. 25, 2019

(30) Foreign Application Priority Data
Sep. 20, 2016    (WO) ................ PCT/CN2016/099474

(51) Int. Cl.
| C07K 16/36 | (2006.01) |
| A61P 7/02 | (2006.01) |
| A61K 9/19 | (2006.01) |
| A61K 39/395 | (2006.01) |
| A61K 39/00 | (2006.01) |

(52) U.S. Cl.
CPC ................ *C07K 16/36* (2013.01); *A61K 9/19* (2013.01); *A61K 39/3955* (2013.01); *A61P 7/02* (2018.01); *A61K 2039/505* (2013.01); *C07K 2317/14* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,510,245 A | 4/1985 | Cousens |
| 4,634,665 A | 1/1987 | Axel |
| 4,968,615 A | 11/1990 | Koszinowski |
| 5,168,062 A | 12/1992 | Stinski |
| 5,179,017 A | 1/1993 | Axel |
| 8,236,316 B2 | 8/2012 | Gruber |
| 9,125,895 B2 | 9/2015 | Gruber |

FOREIGN PATENT DOCUMENTS

| WO | WO2009067660 A2 | 5/2009 |
| WO | WO2010080623 A2 | 7/2010 |
| WO | WO2010080623 A3 | 11/2010 |
| WO | WO2013167669 A1 | 11/2013 |
| WO | WO2016207858 A1 | 12/2016 |
| WO | WO2017015619 A1 | 1/2017 |
| WO | WO2017015619 A8 | 3/2017 |
| WO | WO2017127468 A1 | 7/2017 |

OTHER PUBLICATIONS

Macknnan et al. 'Role of the Extrinsic Pathway of Blood Coagulation in Hemostasis and Thrombosis.' Arterioscler Thromb Vasc Biol. 2007;27:1687-1693.).*
Altschul, S.F. et al. (Oct. 5, 1990). "Basic Local Alignment Search Tool," J. Mol. Biol. 215(3):403-410.
Altschul, S.F.et al. (1997). "Gapped BLAST and PSI-BLAST: A New Generation of Protein Database Search Programs," Nucleic Acids Res. 25(17):3389-3402.
Davie et al. (1991). "The coagulation cascade: Initiation, maintenance, and regulation" Biochem. 43: 10363-10370.
Gailani et al. (1991). "Factor XI activation in a revised model of blood coagulation" Science 253:909-912.
Hwang, W.Y.K. et al. (2005). "Use of human germline genes in a CDR homology-based approach to antibody humanization," Methods 36: 35-42.
International Search Report dated Mar. 29, 2018 for PCT Application No. PCT-EP2017/073410 filed Sep. 18, 2017, 5 pages.
Kaufman, R.J. et al. (1982). "Amplification and Expression of Sequences Cotransfected with a Modular Dihydrofolate Reductase Complementary DNA Gene," J. Mol. Biol. 159:601-621.
Kohler, G. et al. (Aug. 7, 1975) "Continuous Cultures of Fused Cells Secreting Antibody of Predefined Specificity," Nature 256:495-497.
Kravtsov et al. (2009). "Factor XI contributes to thrombin generation in the absence of factor XII" Blood 114:452-458.
McCafferty, J. et al. (Dec. 6, 1990). "Phage Antibodies: Filamentous Phage Displaying Antibody Variable Domains," Nature 348:552-554.
Meijers et al. (2000). "High levels of coagulation factor XI as a risk factor for venous thrombosis" New Engl. J. Med. 342:696-701.

(Continued)

Primary Examiner — Nora M Rooney
(74) Attorney, Agent, or Firm — Morrison & Foerster LLP

(57) ABSTRACT

The present invention in general relates to novel binding molecules, in particular antibodies and compositions and kits comprising the same. Said binding molecules are capable of binding to human Factor XI and hence envisaged to be particularly useful in inhibiting thrombosis without compromising hemostasis. The binding molecules, compositions and kits provided herein are therefore inter alia intended for treatment of thrombosis-related diseases and conditions. Moreover, polynucleotides encoding the binding molecules of the invention, vectors comprising said polynucleotides and host cells for producing the polynucleotides are provided herein.

20 Claims, 11 Drawing Sheets

Specification includes a Sequence Listing.

(56) References Cited

OTHER PUBLICATIONS

Salomon et al (2008). "Reduced incidence of ischemic stroke in patients with severe factor XI deficiency" Blood 111:4113-4117.
Salomon et al. (2011). "Patients with severe factor XI deficiency have a reduced incidence of deep vein thrombosis" Thromb. Haemost. 105:269-273.
Smith et al. (1981). "Identification of Common Molecular Subsequences," J. Mol. Biol. 147: 195-197.
Tom, R. et al. (2007), "Transient expression in HEK293-EBNA1 cells," in Expression Systems: Methods Express, Dyson, M.R. et al. eds., Scion Publishing Ltd: Oxfordshire, pp. 204-223.
Tucker (2009). "Prevention of vascular graft occlusion and thrombus-associated thrombin generation by inhibition of factor XI" Blood 113:936-944.
Van Montfoort, M.L. et al. (2013). "Two novel inhibitory anti-human factor XI antibodies prevent cessation of blood flow in a murine venous thrombosis model," Thrombosis and Haemostasis 110(5): 1065-1073.

\* cited by examiner

Figure 1

SEQ ID NO: 8 (CDR1 LC)
KASQSVLYSGDNYLN

SEQ ID NO: 9 (CDR2 LC)
AASTLES

SEQ ID NO: 10 (CDR3 LC)
QQYNGDPWT

SEQ ID NO: 11 (CDR1 HC)
TSGMGVG

SEQ ID NO: 12 (CDR2 HC)
HIDWDDDKYYSPSLKS

SEQ ID NO: 13 (CDR3 HC)
IRSSVYAHYYGMDY

SEQ ID NO: 17 (VL)
```
DIVMTQSPDS LAVSLGERAT ISCKASQSVL YSGDNYLNWY QQKPGQPPKL LIYAASTLES      60
GIPDRFSGSG SGTDFTLTIS SLQAEDVAVY YCQQYNGDPW TFGGGTKVEI K              111
```

SEQ ID NO: 18 (VH)
```
EVTLRESGPA LVKPTQTLTL TCTFSGFSLS TSGMGVGWIR QPPGKALEWL AHIDWDDDKY      60
YSPSLKSRLT ISKDTSKNQV VLTMTNMDPV DTATYYCARI RSSVYAHYYG MDYWGQGTTV     120
TVSS                                                                 124
```

SEQ ID NO: 27 (LC)
```
DIVMTQSPDS LAVSLGERAT ISCKASQSVL YSGDNYLNWY QQKPGQPPKL LIYAASTLES      60
GIPDRFSGSG SGTDFTLTIS SLQAEDVAVY YCQQYNGDPW TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                            218
```

SEQ ID NO: 28: (HC)
```
EVTLRESGPA LVKPTQTLTL TCTFSGFSLS TSGMGVGWIR QPPGKALEWL AHIDWDDDKY      60
YSPSLKSRLT ISKDTSKNQV VLTMTNMDPV DTATYYCARI RSSVYAHYYG MDYWGQGTTV     120
TVSSASTKGP SVFPLAPSSK STSGGTAALG CLVKDYFPEP VTVSWNSGAL TSGVHTFPAV     180
LQSSGLYSLS SVVTVPSSSL GTQTYICNVN HKPSNTKVDK KVEPKSCDKT HTCPPCPAPE     240
LLGGPSVFLF PPKPKDTLMI SRTPEVTCVV VDVSHEDPEV KFNWYVDGVE VHNAKTKPRE     300
EQYNSTYRVV SVLTVLHQDW LNGKEYKCKV SNKALPAPIE KTISKAKGQP REPQVYTLPP     360
SRDELTKNQV SLTCLVKGFY PSDIAVEWES NGQPENNYKT TPPVLDSDGS FFLYSKLTVD     420
KSRWQQGNVF SCSVMHEALH NHYTQKSLSL SPG                                 453
```

Figure 9

| designation | EC50 ELISA [nM] (human FXI) | EC50 ELISA [nM] (baboon FXI) | EC50 [nM] Conversion Assay (human FXI) | aPTT 1,5 X [nM] |
|---|---|---|---|---|
| 1A6 | 0.15 +/- 0.03 | 0.16 +/- 0.02 | 0.5 +/- 0.03 | 7 |
| TPP-3583 | 0.2 +/- 0.02 | 0.13 +/- 0.02 | 0.6 +/- 0.04 | 5 |
| TPP-3577 | 0.19 +/- 0.02 | 0.16 +/- 0.02 | 0.4 +/- 0.02 | 11 |
| TPP-3290 | 0.17 +/- 0.03 | 0.14 +/- 0.02 | 0.4 +/- 0.02 | 93 |
| TPP-3238 | 0.16 +/- 0.02 | 0.28 +/- 0.02 | 0.6 +/- 0.03 | > 500 |

# ANTIBODIES AGAINST FACTOR XI AND USES THEREOF

CROSS REFERENCE TO RELATED APPLICATIONS

This application is a national stage application under 35 U.S.C. § 371 of International Application No. PCT/EP2017/073410, filed internationally on Sep. 18, 2017 which claims the benefit of priority to International Application No. PCT/CN2016/099474, filed internationally on Sep. 20, 2016.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 777052032700SEQLIST.TXT, date recorded: Mar. 19, 2019, size: 45 KB).

BACKGROUND

Thromboembolic disorders, including both venous and arterial thrombosis, are a major cause of morbidity and mortality worldwide. They are caused by dysregulation of normal blood coagulation (hemostasis) leading to abnormal formation of clots (thrombi) from fibrin, eventually resulting in tissue ischemia and, in some circumstances, embolization due to dislodging and migration of clot fragments from the thrombus.

Under normal circumstances, hemostasis is a vital mechanism that prevents blood loss from sites of vascular injury by inducing platelet activation and formation of fibrin. On a mechanistic level, hemostasis proceeds in two steps. During primary hemostasis platelets adhere to the site of trauma and become activated, and ultimately aggregate by binding to each other to form a platelet plug. Platelet plug formation is enhanced and stabilized during secondary hemostasis—a series of enzymatic reactions involving coagulation proteins (also called blood coagulation system) that culminate in formation of the protease thrombin, which converts fibrinogen to fibrin to form a stable clot that seals a breach in blood vessel walls.

Since 1964, when Macfarlane (Nature. 1964 May 2; 202:498-9) introduced the cascade hypotheses for the process of blood coagulation, the knowledge of the function of blood coagulation in vivo has grown. In the last years, the theory of two distinct routes, the so called the extrinsic and intrinsic pathway, that initiate coagulation and converge in a common pathway, ultimately leading to thrombin generation and fibrin deposition, has been revised.

In the current model initiation of coagulation occurs when the plasma protease activated factor VII comes into contact and thereby forms a complex with Tissue Factor (TF). This Tissue Factor-FVIIa complex converts the zymogen FX to its active form FXa, which in turn cleaves prothrombin (coagulation factor II) to form thrombin (IIa) in the presence of the cofactor FVa. Thrombin, a key player in coagulation, in turn can catalyze the conversion of fibrinogen into fibrin. Additionally, thrombin activates specific receptors expressed by platelets, which leads to the activation of the latter. Activated platelets in combination with fibrin are essential for clot formation and therefore are fundamental players of normal hemostasis. The FVIIa-TF complex also converts FIX to the protease FIXa, which, in the presence of FVIIIa, activates additional FX to sustain thrombin production.

The coagulation pathway involves the coagulation factor XI (FXI). It is well confirmed that FXI is, like the other members of the coagulation cascade, a plasma serine protease zymogen with a key role in bridging the initiation phase and the amplification phase of blood coagulation in vivo (Davie E W et al., Biochemistry. 1991 Oct. 29; 30(43): 10363-70, Gailani D and Broze G J Jr., Science. 1991 Aug. 23; 253(5022):909-12; Kravtsov D V et al. Blood. 2009 Jul. 9; 114(2):452-8).

Interestingly, FXI deficiency usually does not lead to spontaneous bleeding, but is associated with increased risk of bleeding with hemostatic challenges, although the severity of bleeding correlates poorly with the plasma level of FXI. Severe FXI deficiency in humans has been reported to have certain protective effects from thrombotic diseases, including ischemic stroke and deep venous thrombosis (DVT) (Salomon O et al, Thromb Haemost. 2011 February; 105(2):269-73; Salomon O et al, Blood. 2008 Apr. 15; 111(8):4113-7). Yet, a high level of FXI has been associated with thrombotic events and has been reported to confer higher risk for DVT, myocardial infarction (MI), and stroke (Meijers J C et al, N Engl J Med. 2000 Mar 9; 342(10): 696-701).

Taken together, previous studies suggest that FXI has a minor supporting role in maintaining hemostasis but is a crucial contributor to the pathogenesis of thrombosis, thereby rendering FXI a promising target for antithrombotic therapy. This is so because, although thrombosis and hemostasis are not identical molecular processes, they are similar enough that currently used antithrombotic drugs inadvertently target both. Presently available antithrombotic drugs either target the building blocks of thrombi (fibrin and platelets) or inhibit molecules (coagulation factors) and cells (platelets) from participating in the thrombus-forming process. Antiplatelet, profibrinolytic and anticoagulant agents have been the mainstay for the treatment and prevention of thromboembolic diseases for decades and are among the most commonly prescribed drugs in clinical practice. Yet, most of these agents can completely block both thrombosis and hemostasis when administered in effective doses.

So far, one of the few examples for an anti-FXI antibody exhibiting therapeutic potential is murine antibody 1A6 (also named aXIMab) as published by Tucker et al. (Prevention of vascular graft occlusion and thrombus-associated thrombin generation by inhibition of factor XI. Erik I. Tucker, Ulla M. Marzec, Tara C. White, Sawan Hurst, Sandra Rugonyi, Owen J. T. McCarty, David Gailani, András Gruber, and Stephen R. Hanson. Blood. 2009 Jan. 22; 113(4):936-944). Antibody 1A6 is also disclosed in patent application WO 2009/067660 A2, also published as U.S. Pat. No. 9,125,895, which is incorporated herein by reference in its entirety. However, as antibody 1A6 is a murine antibody, it is unsuitable for human therapies especially for chronic applications as such as antithrombotic therapy. One method to convert a murine antibody into an acceptable therapeutic antibody is so-called humanization. Standard techniques are available to the person skilled in the art such as those described in O'Brien and Jones, Humanising Antibodies by CDR Grafting, Chapter 40; Antibody Engineering, Part of the series Springer Lab Manuals pp 567-590; R. Kontermann et al. (eds.), Antibody Engineering; Springer-Verlag Berlin Heidelberg 2001 and in Hwang, Almagro, Buss, Tan, and Foote (2005) Use of human germline genes in a CDR homology-based approach to antibody humanization. Methods, May; 36(1):35-42 and in the references therein. For further reduction of the inherent immunogenicity potential of humanized antibodies, further sequence optimization and germlining is required.

When Applicants applied these standard methods to humanize and optimize parenteral antibody 1A6, some of the resulting antibodies exhibited binding activity in a biochemical assay comparable to the parenteral 1A6, however, showed a significant loss of activity in plasma based assays and were inadequate in in vivo models of coagulation. Thus far, there is no explanation readily available why a comparable biochemical profile of the parental murine antibody 1A6 and humanized variants does not translate into efficient anti-thrombotic activity. Surprisingly, by introduction of further sequence alterations a humanized variant of parental murine antibody 1A6 has been generated (antibody TPP-3583) which display both a comparable biochemical profile and anti-thrombotic efficacy in vivo.

With the antibodies of this invention, therapeutic molecules have been generated which have a reduced immunogenicity risk and effectively block thrombosis without debilitating hemostasis, thereby making antithrombotic therapy safer, and thus broadening the range of clinical indications and scenarios in which antithrombotic therapy can be applied.

SUMMARY

In a first aspect, the present invention provides a binding molecule comprising

```
a CDR1 of the light chain comprising the sequence
                                       (SEQ ID NO: 8)
KASQSVLYSGDNYLN;

a CDR2 of the light chain comprising the sequence
                                       (SEQ ID NO: 9)
AASTLES;

a CDR3 of the light chain comprising the sequence
                                       (SEQ ID NO: 10)
QQYNGDPWT;

a CDR1 of the heavy chain comprising the sequence
                                       (SEQ ID NO: 11)
TSGMGVG;

a CDR2 of the heavy chain comprising the sequence
                                       (SEQ ID NO: 12)
HIDWDDDKYYSPSLKS;
and a CDR3 of the heavy chain comprising the sequence
                                       (SEQ ID NO: 13)
IRSSVYAHYYGMDY.
```

The binding molecule may comprise a VL region as depicted in SEQ ID NO: 17 and/or a VH region as depicted in SEQ ID NO: 18.

Said binding molecule is envisaged to be capable of binding to factor XI and/or factor XIa, in particular to a human or non-human primate factor XI or a human or non-human primate factor XIa.

Specifically, the binding molecule is envisaged to bind within an amino acid sequence corresponding to the A3 domain of factor XI comprising amino acids 200 to 283 of SEQ ID NO: 7 and particularly to a domain within an amino acid sequence corresponding to a) amino acids 200 to 215 of SEQ ID NO: 7; b) amino acids 221 to 222 of SEQ ID NO: 7; c) amino acids 252 to 254 of SEQ ID NO: 7; d) amino acids 259 to 261 of SEQ ID NO: 7; e) amino acids 270 to 272 of SEQ ID NO: 7; and f) amino acids 276 to 278 of SEQ ID NO: 7. Here numbering of the amino acids of human factor XI includes the signal sequence starting with methionine at position 1. It is contemplated that said binding molecule may be an antibody, and specifically a humanized monoclonal antibody or antigen-binding fragment thereof, for example being an IgG antibody.

In a further aspect, the present invention provides a polynucleotide encoding a binding molecule as defined herein, and a vector, particularly an expression vector, comprising said polynucleotide. The invention also relates to a host cell comprising said vector or polynucleotide.

In a further aspect, a process for the production of a binding molecule as described herein is provided, said process comprising culturing a host cell as defined herein under conditions allowing the expression of said binding molecule and optionally recovering the produced binding molecule from the culture.

Moreover, the invention relates to a pharmaceutical composition comprising a binding molecule, polynucleotide, the vector and/or the host cell as defined herein, and optionally a pharmaceutically acceptable excipient. Said pharmaceutical composition may comprise additional active agents, in particular anti-thrombotic and/or anti-coagulant agents or be administered as part of combination therapy with additional active agents.

According to the present invention, the binding molecule, polynucleotide, vector, host cell or the pharmaceutical composition can be used in a method of inhibiting blood coagulation, platelet aggregation and/or thrombosis in a subject, and are therefore envisaged for use in the treatment and/or prophylaxis of disorders, in particular cardiovascular disorders, preferably thrombotic or thromboembolic disorders and/or thrombotic or thromboembolic complications.

Further provided herein is the use of the binding molecule as an anticoagulant in blood samples, blood preservations, plasma products, biological samples, or medicinal additives or as a coating on medical devices.

Moreover, the present invention relates to a kit comprising a binding molecule, polynucleotide, vector, host cell or the pharmaceutical composition as described herein.

DESCRIPTION OF THE FIGURES

FIG. 1: Sequences of the anti-FXI antibody TPP-3583.

FIG. 9: Listing of EC50 values and aPTT values for certain antibodies.

DETAILED DESCRIPTION

Figure 2:
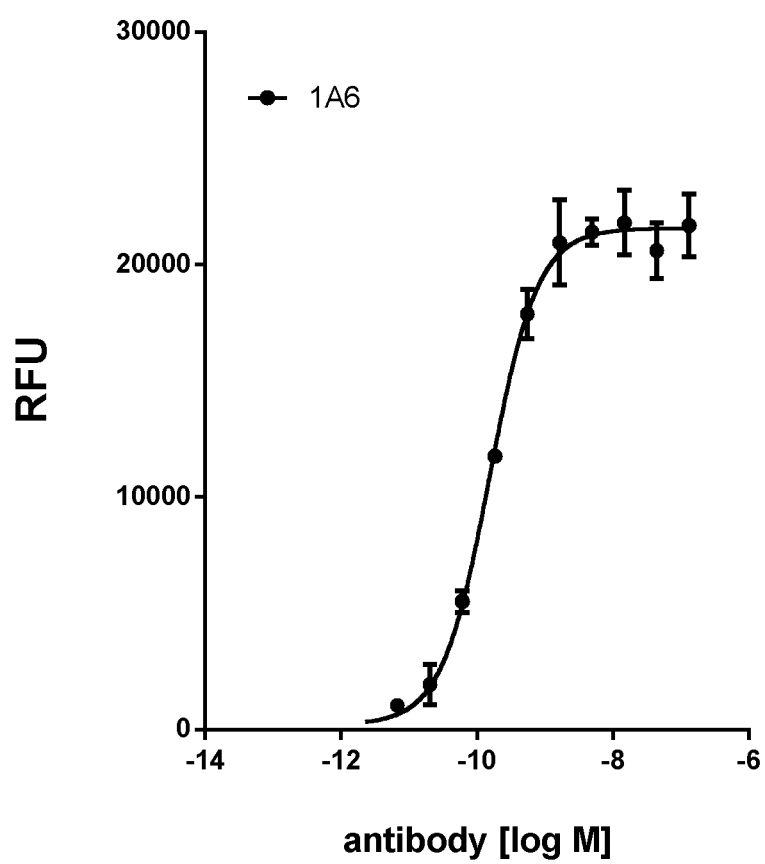
FIG. 2: Binding activities (EC50 value) of the murine anti-FXI antibody 1A6 to the human coagulation factor XI (FXI).

Inhibition of FXI—which is ascribed a critical role in development of pathological thrombus formation, while having limited (or no effect) on physiologic hemostasis—is a promising novel approach in the development of new anti-thrombotic agents to achieve an improved benefit-risk ratio. The present invention, inter alia, provides novel binding molecules that are capable of specifically binding to FXI, thereby inhibiting FXI conversion into its activated form FXIa. Moreover, the binding molecules have also been shown to bind to FXIa. The binding molecules provided herein are, thereby, thought to block the activation of downstream players involved in blot clotting and thrombosis. Specifically, the present inventors provided humanized versions of the murine 1A6 anti-FXI antibody that, advantageously, bind to FXI and also FXIa with a high binding affinity comparable to 1A6. Moreover, the binding molecules effectively reduce blot clotting, as indicated by their capability of prolonging the activated partial thromboplastin time (aPTT) at low concentrations. The binding molecules of the present invention are therefore promising new agents for effective treatment and/or prophylaxis of thrombotic or thromboembolic disorders and/or thrombotic or thromboembolic complications and are moreover thought to be effective without severely compromising hemostasis, thereby minimizing the risk of bleeding.

Binding Molecule

The binding molecules of the present invention were obtained by humanization and subsequent CDR optimization of the murine anti-FXI antibody 1A6 as disclosed in WO 2009/067660 A2. Much to their surprise, the present inventors found that binding molecules comprising a number of amino acid substitutions in their CDR regions as compared to the 1A6 CDRs exhibited advantageous properties. Binding molecules of the invention are capable of binding to FXI with binding affinities comparable to 1A6, and inhibit its conversion into its active form FXIa, and effectively reduced blot clotting. In contrast, other candidate binding molecules having less or more amino acid substitutions did not exhibit the same advantageous properties.

Therefore, the present invention, in a first aspect, relates to binding molecules capable of specifically binding to factor XI which binding molecules comprise the following complementarity determining regions (CDRs):

a) CDR1 of the light chain:
(SEQ ID NO: 1)
KASQSVDYDGDSYLN, b) CDR2 of the light chain:
(SEQ ID NO: 2)
AASNLES, c) CDR3 of the light chain:
(SEQ ID NO: 3)
QQSNGDPWT, d) CDR1 of the heavy chain:
(SEQ ID NO: 4)
TSGMGVG, e) CDR2 of the heavy chain:
(SEQ ID NO: 5)
HIWWDDDKYYNPSLKS,
and f) CDR3 of the heavy chain:
(SEQ ID NO: 6)
KRSSVVAHYYAMD, wherein said CDRs are characterized in that at least two CDRs cumulatively comprises 10, 11, 12, 13 or 14 amino acid substitutions.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr).

Number and Distribution of Substitutions

The amino acid substitutions can generally be distributed across the CDRs in any way, i.e. one CDR may for instance comprise one exchange, and a second CDR may comprise 9, 10, 11, 12 or 13 substitutions. Or two CDRs may comprise 5 amino acid substitutions, or all six CDRs may comprise amino acid substitutions, e.g. two substitutions per CDR. Particularly envisaged herein are binding molecules comprising at least 5 amino acid substitutions in the CDR1, CDR2 and/or CDR3 of the light chain and at least 5 amino acid substitutions in CDR1, CDR2 and/or CDR3 of the heavy chain. Generally, the amino acid substitutions can be distributed virtually in any manner, as long as the number of cumulative amino acid substitutions as compared to the 1A6 CDR amino acid sequences ranges between 10 and 14 (i.e. including 10, 11, 12, 13 or 14) and preferably does not abolish the binding molecule's capability to bind to factor XI.

Type of Substitutions

In general, any combination of amino acid substitutions in the CDRs as compared to 1A6 is conceivable as long as it doesn't abolish the advantageous properties of the binding molecules of the invention. Amino acid exchanges can be conservative (i.e. exchanging an amino acid of one class or group for another amino acid from the same class or group as listed above) or non-conservative (i.e. exchanging an amino acid from one class/group for another amino acid from another class/group).

Particular amino acid substitutions that are envisaged in accordance with the present invention include the following:
(a) $D_8 \rightarrow L_8$, $D_{11} \rightarrow S_{11}$ and/or $S_{14} \rightarrow N_{14}$ with respect to SEQ ID NO: 1;
(b) $N_6 \rightarrow T_6$ with respect to SEQ ID NO: 2;
(c) $S_5 \rightarrow Y_5$ with respect to SEQ ID NO: 3;
(d) $G_{12} \rightarrow C_{12}$ with respect to SEQ ID NO: 4;
(e) $W_5 \rightarrow D_5$, $N_{13} \rightarrow S_{13}$ with respect to SEQ ID NO: 5;
(f) $K_3 \rightarrow I_3$, $V_8 \rightarrow Y_8$, $A_{13} \rightarrow G_{13}$ and/or $Y_{16} \rightarrow V_{16}$ with respect to SEQ ID NO: 6

Preferred substitutions yield binding molecules of the present invention which lead to a 1.5 fold prolongation of the aPTT (as described elsewhere herein) at a concentration of 0.03 µM or less, or 0.015 µM or less, or 0.01 µM or less.

In particular, binding molecules of the invention may comprise the following CDRs:

```
(a) a CDR1 of the light chain comprising the
sequence
                                           (SEQ ID NO: 8)
KASQSVLYSGDNYLN
or (SEQ ID NO: 14)
KSSQSVLYSGDNYLN,
with SEQ ID NO: 8 being preferred;
and/or (b) a CDR2 of the light chain comprising the
sequence
                                           (SEQ ID NO: 9)
AASTLES;
and/or (c) a CDR3 of the light chain comprising the
sequence
                                          (SEQ ID NO: 10)
QQYNGDPWT;
and/or (d) a CDR1 of the heavy chain comprising the
sequence
                                          (SEQ ID NO: 11)
TSGMGVG;
and/or (e) a CDR2 of the heavy chain comprising the
sequence
                                          (SEQ ID NO: 12)
HIDWDDDKYYSPSLKS
or (SEQ ID NO: 15)
HIDWDDDKYYSTSLKS,
with SEQ ID NO: 12 being preferred;
and/or (f) a CDR3 of the heavy chain comprising the
sequence
                                          (SEQ ID NO: 13)
IRSSVYAHYYGMDY
or (SEQ ID NO: 16)
IRSSVYAHYYGMDV,
with SEQ ID NO: 13 being preferred.
```

As it is apparent from the above, binding molecules according to the invention may comprise one or more of the aforementioned CDRs, optionally in combination.

A particularly preferred binding molecule according to the invention, which may be a monoclonal antibody or antigen-binding fragment thereof, comprises the following CDRs: a CDR1 of the light chain comprising the sequence KASQSVLYSGDNYLN (SEQ ID NO: 8); a CDR2 of the light chain comprising the sequence AASTLES (SEQ ID NO: 9); a CDR3 of the light chain comprising the sequence QQYNGDPWT (SEQ ID NO: 10); a CDR1 of the heavy chain comprising the sequence TSGMGVG (SEQ ID NO: 11); a CDR2 of the heavy chain comprising the sequence HIDWDDDKYYSPSLKS (SEQ ID NO: 12); and a CDR3 of the heavy chain comprising the sequence IRSSVYAHYYGMDY (SEQ ID NO: 13). A further particularly preferred binding molecule according to the invention, which may be a monoclonal antibody or antigen-binding fragment thereof, comprises the following CDRs: a CDR1 of the light chain consisting of the sequence KASQSVLYSGDNYLN (SEQ ID NO: 8); a CDR2 of the light chain consisting of the sequence AASTLES (SEQ ID NO: 9); a CDR3 of the light chain consisting of the sequence QQYNGDPWT (SEQ ID NO: 10); a CDR1 of the heavy chain consisting of the sequence TSGMGVG (SEQ ID NO: 11); a CDR2 of the heavy chain consisting of the sequence HIDWDDDKYYSPSLKS (SEQ ID NO: 12); and a CDR3 of the heavy chain consisting of the sequence IRSSVYAHYYGMDY (SEQ ID NO: 13).

Moreover, binding molecules of the invention are envisaged to comprise a variable region of the light chain ($V_L$ or VL region) as depicted in SEQ ID NO: 17 or SEQ ID NO: 19, with a VL region as depicted in SEQ ID NO: 17 being preferred, and/or a variable region of the heavy chain ($V_H$ or VH region) as depicted in SEQ ID NO: 18 or SEQ ID NO: 20, with a $V_H$ region as depicted in SEQ ID NO: 18 being preferred. Accordingly, preferred binding molecules of the invention comprise a $V_L$ region as depicted in SEQ ID NO: 17 and a $V_H$ region as depicted in SEQ ID NO: 18. However, other combinations of $V_L$ and $V_H$ regions disclosed herein are also conceivable. Accordingly, a preferred embodiment is humanized monoclonal antibody TPP-3583 with sequences as depicted in FIG. 1.

Factor XI

As set out previously herein, the binding molecules of the invention are preferably capable of binding to factor XI.

"Factor XI", also referred to herein as "coagulation factor XI", "FXI or "fXI" is a two-chain glycoprotein with a molecular weight of approximately 160 kilo Daltons (kD). The two chains are identical disulfide bonded polypeptides with molecular weights of approximately 80,000 daltons. FXI contains 4 "apple domains" (A1 to A4 from the N-terminus, heavy chain) and a C-terminal catalytic domain (light chain). Without wishing to be bound by specific theory, it is thought that the 4 apple domains contain the FXI binding sites for other proteins, such as A1 for thrombin; A2 for HK, A3 for factor IX (FIX), GPIb, and heparin, and A4 for FXIIa. FXI can be converted into its active form, the coagulation factor XIa (FXIa) by Factor XIIa (FXIIa). The serine protease FXIa converts the coagulation Factor IX into IXa, which subsequently activates coagulation Factor X (Xa). Xa then can mediate coagulation Factor II/Thrombin activation.

In particular, the term "Factor XI" refers to the human coagulation factor XI with Uniprot Acc. No. P03951, entry version 194 of 14 Oct. 2015 (SEQ ID NO: 7). As set out elsewhere herein, the binding molecules of the invention are particularly envisaged to bind to an domain within an amino acid sequence corresponding to amino acids 200 to 283 of SEQ ID NO: 7. Numbering of the amino acids of human FXI includes the signal sequence starting with the amino acid methionine at position 1.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids, but is rather to be viewed in the context of the circumjacent portion of the sequence. Accordingly, the position of a given amino acid or nucleotide in accordance with the disclosure may vary due to deletion or addition of amino acids or nucleotides elsewhere in the sequence. Thus, when a position is referred to as a "corresponding position" in accordance with the disclosure it is understood that nucleotides/amino acids may differ in terms of the specified numeral but may still have similar neighboring nucleotides/amino acids. In order to determine whether an amino acid residue (or nucleotide) in a given sequence corresponds to a certain position in the amino acid sequence (or polynucleotide sequence) of a "parent" amino acid (or polynucleotide sequence) (e.g. that of human FXI as depicted in SEQ ID NO: 7), the skilled person can use means and methods well-known in the art, e.g., sequence alignments, either manually or by using computer programs as exemplified herein.

The term "epitope" in general refers to a site on an antigen, typically a (poly-)peptide, which a binding domain recognizes, and can also be referred to as an "antigenic structure" or "antigenic determinant". The term "binding domain" refers to an "antigen binding site", i.e. characterizes a domain of a binding molecule which binds/interacts with a given target epitope on an antigen or a group of antigens, e.g. the identical antigen in different species. A target antigen may comprise a single epitope, but typically comprises at least two epitopes, and can include any number of epitopes, depending on the size, conformation, and type of antigen. Furthermore, it should be noted that an "epitope" on a target antigen is typically a target (poly-)peptide, but may also be or include non-polypeptide elements, e.g., an epitope may include a carbohydrate side chain. The term "epitope" in general encompasses linear epitopes and conformational epitopes. Linear epitopes are contiguous epitopes comprised in the amino acid primary sequence and typically include at least 2 amino acids or more. Conformational epitopes are formed by non-contiguous amino acids juxtaposed by folding of the target antigen, and in particular target (poly-)peptide.

Binding molecules of the present invention are envisaged to recognize epitopes located on the heavy chain of factor XI that contain a sequence of at least 2, at least 3, at least 4, at least 5, at least 6, at least 7, at least 8, at least 9, at least 10 contiguous or noncontiguous amino acids of factor XI (SEQ ID NO: 7).

It is in particular envisaged that the binding molecules provided herein bind to the A3 domain of human factor XI which comprises amino acids 200 to 283 of SEQ ID NO: 7.

However, it is also envisaged that the binding molecules may be capable of binding to variants of human FXI as specified above. The term "variant" when used in relation to FXI refers to a polypeptide comprising one or more amino acid sequence substitutions, deletions, and/or additions as compared to a "parent" FXI sequence and exerts the same biologic function, i.e. can be converted to its active form FXIa which has serine protease activity and catalyzes the activation of factor IX, thereby triggering the intrinsic pathway of blood coagulation. Amino acid substitutions may be conservative, as defined herein, or non-conservative or any combination thereof. FXI variants may have additions of amino acid residues either at the carboxy terminus or at the amino terminus (where the amino terminus may or may not comprise a leader sequence). In particular, the term "variant" when used in relation to FXI includes isoforms, allelic or splice variants, or post-translationally modified variants (e.g. glycosylation variants) of known FXI polypeptides, for instance of a FXI polypeptide having a sequence as depicted in SEQ ID NO: 7. It will be readily understood that the binding molecules of the invention may particularly exhibit a binding affinity towards FXI variants comprising an amino acid sequence corresponding to amino acids 200 to 283 of SEQ ID NO: 7, or specifically an amino acid sequence corresponding to a) amino acids 201 to 215 of SEQ ID NO: 7; b) amino acids 221 to 222 of SEQ ID NO: 7; c) amino acids 252 to 254 of SEQ ID NO: 7; d) amino acids 259 to 261 of SEQ ID NO: 7; e) amino acids 270 to 273 of SEQ ID NO: 7; and/or f) amino acids 276 to 278 of SEQ ID NO: 7. In accordance with the foregoing, it is also envisaged that the binding molecules are also capable of binding to FXIa and variants thereof, provided that they comprise at least one of the aforementioned amino acid stretches or amino acid positions corresponding thereto.

Binding molecules of the invention may also be capable of binding to FXI from other mammalian species, preferably non-human primate species. These non-human FXI polypeptides are preferably encoded by an FXI gene or ortholog or paralog thereof and exhibit the same biological function as human FXI. Potential non-human primate protein targets of the binding molecules of the invention include polypeptides with Uniprot Acc No. H2QQJ4 (*Pan troglodytes*, entry version 26 of 11 Nov. 2015), Uniprot Acc. No. H2PEX7 (*Pongo abelii*, entry version 27 of 11 Nov. 2015), Uniprot Acc. No. A0A0D9S2M6 (*Chlorocebus sabaeus*, entry version 6 of 11 Nov. 2015), UniProt Acc. No. G3R2X1 (*Gorilla gorilla gorilla*, entry version 27 of 14 Oct. 2015), Uniprot Acc. No. A0A096NC95 (*Papio anubis*, entry version 11 of 11 Nov. 2015), Uniprot Acc. No. G1RLE8 (*Nomascus leucogenys*, entry version 28 of 11 Nov. 2015), Uniprot Acc. No. G7PKF5 (*Macaca fascicularis*, entry version 13 of 14 Oct. 2015), UniProt Acc. No. G7MSF8 (*Macaca mulatta*, entry version 12 of 14 Oct. 2015). Variants of the aforementioned polypeptides are also envisaged as targets for the binding molecules of the invention. Envisaged non-human primate polypeptide targets recognized by the binding molecules of the invention are particularly envisaged to comprise a sequence corresponding to amino acids 200 to 283 of SEQ ID NO: 7, and/or an amino acid sequence corresponding to a) amino acids 201 to 215 of SEQ ID NO: 7; b) amino acids 221 to 222 of SEQ ID NO: 7; c) amino acids 252 to 254 of SEQ ID NO: 7; d) amino acids 259 to 261 of SEQ ID NO: 7; e) amino acids 270 to 273 of SEQ ID NO: 7; and/or f) amino acids 276 to 278 of SEQ ID NO: 7 or a sequence having at least 95%, 96%, 97%, 98%, or 99% sequence identity thereto. Thus, cross-species specific binding molecules directed against FXI, particularly in non-human primates, are also provided herein. The term "cross-species recognition" or "interspecies specificity" as used herein thus means binding of a binding molecule described herein to the same target polypeptide in humans and non-human, particularly non-human primate, species.

As set out previously, it is envisaged that the binding molecules described herein are also capable of binding to human or non-human primate Factor XIa. Thus, what is disclosed in the context of the binding molecule's binding characteristics as to Factor XI is preferably equally applicable to its binding characteristics as to Factor XIa, mutatis mutandis.

Antibody

The binding molecule of the invention is in particular envisaged to be an antibody. As is well known in the art, an antibody is an immunoglobulin molecule capable of specific binding to a target epitope through at least one epitope recognition site, located in the variable region of the immunoglobulin molecule. The terms "antibody", "antibody molecule" and "immunoglobulin" are used interchangeably and in their broadest sense herein and include native antibodies, monoclonal antibodies, polyclonal antibodies, multispecific antibodies (e.g., bispecific antibodies), (naturally occurring or synthetic) antibody derivatives, fragments or variants, fusion proteins comprising an antigen-binding fragment of the required specificity and any other modified configuration of the antibody that comprises an antigen-binding site of the required specificity. Antibodies according to the invention are envisaged to be capable of binding to FXI as described elsewhere herein, and preferably exhibit the advantageous characteristics of the antibodies TTP-3583 and TTP-3577 as set out in the appended examples.

Native Antibody

A "native antibody" is a tetrameric glycoprotein. In a naturally-occurring native antibody, each tetramer is composed of two identical pairs of polypeptide chains, each pair having one "light" chain (about 25 kDa) and one "heavy" chain (about 50-70 kDa). The amino-terminal portion of each chain includes a "(hyper)variable" region of about 100 to 110 or more amino acids primarily responsible for antigen recognition. The hypervariable region comprises amino acid residues from a "complementarity determining region" or CDRs or "CDR regions". "Framework" or FR residues are those variable domain residues other than the hypervariable region residues.

Both the light and heavy chains are divided into regions of structural and functional homology referred to as the "constant region" and the "variable region." The terms "constant" and "variable" are used functionally. In this regard, it will be appreciated that the variable regions of both the light ($V_L$) and heavy ($V_H$) chains determine antigen recognition and specificity. The terms "$V_L$", "$V_L$ region", and "$V_L$ domain" are used interchangeably throughout the specification to refer to the variable region of the light chain. Similarly, the terms "$V_H$", "$V_H$ region" and "$V_H$ domain" are used interchangeably herein to refer to the variable region of the heavy chain.

The terms "$C_L$", $C_L$ region" and "$C_L$ domain" are used interchangeably herein to refer to the constant region of the light chain. The terms "$C_H$", $C_H$ region" and "$C_H$ domain" are used interchangeably herein to refer to the constant region of the heavy chain and comprises the "$C_{H1}$", $C_{H2}$", and "$C_{H3}$" regions or domains. Conversely, the constant domains of the light chain ($C_L$) and the heavy chain ($C_{H1}$, $C_{H2}$, or $C_{H3}$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_{H3}$ and $C_L$ regions actually comprise the carboxy-terminus of the heavy and light chain, respectively.

As indicated above, the variable region allows the antibody to selectively recognize and specifically bind epitopes on antigens. That is, the $V_L$ and $V_H$ region, or the subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs (CDR1, CDR2, CDR3, determined following Kabat numbering system) on each of the $V_H$ and $V_L$ regions. The three CDRs of the light chain are also designated CDR1 LC or $CDR_{L1}$, CDR2 LC or $CDR_{L2}$ and CDR3 LC or $CDR_{L3}$ herein. The three CDRs of the heavy chain are termed CDR1 HC or $CDR_{H1}$, CDR2 HC or $CDR_{H2}$ and CDR3 HC or $CDR_{H3}$. In native antibodies, the six "complementarity determining regions" or "CDRs" or "CDR regions" present in each antigen binding domain are typically short, non-contiguous sequences of amino acids that are specifically positioned to form the antigen binding domain as the antibody assumes its three dimensional configuration in an aqueous environment.

As set out previously herein, binding molecules and, in particular, antibodies of the invention are envisaged to comprise a CDR1 of the light chain comprising or consisting of the sequence KASQSVLYSGDNYLN (SEQ ID NO: 8) or KSSQSVLYSGDNYLN (SEQ ID NO: 14), with SEQ ID NO: 8 being preferred; and/or a CDR2 of the light chain comprising or consisting of the sequence AASTLES (SEQ ID NO: 9); and/or a CDR3 of the light chain comprising or consisting of the sequence QQYNGDPWT (SEQ ID NO: 10); and/or a CDR1 of the heavy chain comprising or consisting of the sequence TSGMGVG (SEQ ID NO: 11); and/or a CDR2 of the heavy chain comprising or consisting of the sequence HIDWDDDKYYSPSLKS (SEQ ID NO: 12) or HIWWDDDKYYNPSLKS (SEQ ID NO: 15) with SEQ ID NO: 12 being preferred; and/or a CDR3 of the heavy chain comprising or consisting of the sequence IRSSVYAHYYGMDY (SEQ ID NO: 13) or IRSSVYAHYYG-MDV (SEQ ID NO: 16), with SEQ ID NO:13 being preferred.

A particularly preferred binding molecule according to the invention, which may be a monoclonal antibody or antigen-binding fragment thereof, comprises the following CDRs: a CDR1 of the light chain comprising or consisting of the sequence KASQSVLYSGDNYLN (SEQ ID NO: 8); a CDR2 of the light chain comprising or consisting of the sequence AASTLES (SEQ ID NO: 9); a CDR3 of the light chain comprising or consisting of the sequence QQYNGDPWT (SEQ ID NO: 10); a CDR1 of the heavy chain comprising or consisting of the sequence TSGMGVG (SEQ ID NO: 11); a CDR2 of the heavy chain comprising or consisting of the sequence HIDWDDDKYYSPSLKS (SEQ ID NO: 12); and a CDR3 of the heavy chain comprising or consisting of the sequence IRSSVYAHYYGMDY (SEQ ID NO: 13), all of which are depicted in FIG. 1. The skilled person will readily understand that the CDRs are located in the variable region of the light and heavy chain, respectively. A particularly preferred embodiment of the invention is an antibody or antigen-binding fragment thereof comprising an antigen-binding site of the light chain that comprises a CDR1 of the light chain comprising the sequence as depicted in SEQ ID NO: 8; a CDR2 of the light chain comprising the sequence as depicted in SEQ ID NO: 9; and a CDR3 of the light chain comprising the sequence as depicted in SEQ ID NO: 10; and an antigen-binding site of the heavy chain that comprises a CDR1 of the heavy chain comprising the sequence as depicted in SEQ ID NO: 11; a CDR2 of the heavy chain comprising the sequence as depicted in SEQ ID NO: 12; and a CDR3 of the heavy chain comprising the sequence as depicted in SEQ ID NO: 13. A further particularly preferred embodiment of the invention is an antibody or antigen-binding fragment thereof comprising an antigen-binding site of the light chain that comprises a CDR1 of the light chain consisting of the sequence as depicted in SEQ ID NO: 8; a CDR2 of the light chain consisting of the sequence as depicted in SEQ ID NO: 9; and a CDR3 of the light chain consisting of the sequence as depicted in SEQ ID NO: 10; and an antigen-binding site of the heavy chain that comprises a CDR1 of the heavy chain consisting of the sequence as depicted in SEQ ID NO: 11; a CDR2 of the heavy chain consisting of the sequence as depicted in SEQ ID NO: 12; and a CDR3 of the heavy chain consisting of the sequence as depicted in SEQ ID NO: 13. A monoclonal antibody comprising the aforementioned CDRs is evaluated in the appended Examples and designated "TTP-3583" herein.

Binding molecules and, in particular, antibodies of the invention are envisaged to comprise a $V_L$ region as depicted in SEQ ID NO: 17 or SEQ ID NO: 19, with a $V_L$ region as depicted in SEQ ID NO: 17 being preferred, and/or a $V_H$ region as depicted in SEQ ID NO: 18 or SEQ ID NO: 20, with a $V_H$ region as depicted in SEQ ID NO: 18 being preferred. Accordingly, preferred antibodies of the invention comprise a $V_L$ region as depicted in SEQ ID NO: 17 and a $V_H$ region as depicted in SEQ ID NO: 18. However, other combinations of $V_L$ and $V_H$ regions disclosed herein are also conceivable.

Binding molecules and, in particular, antibodies of the invention are envisaged to comprise a light chain as depicted in SEQ ID NO: 27 or SEQ ID NO: 29, with a light chain as depicted in SEQ ID NO: 27 being preferred, and/or a heavy chain as depicted in SEQ ID NO: 28 or SEQ ID NO: 30, with a heavy chain as depicted in SEQ ID NO: 28 being preferred. Accordingly, preferred antibodies of the invention comprise a light chain as depicted in SEQ ID NO: 27 and a heavy chain as depicted in SEQ ID NO: 28. However, other combinations of light and heavy chains disclosed herein are also conceivable.

A particularly preferred embodiment of the invention is a monoclonal antibody or antigen-binding fragment thereof comprising a $V_L$ region as depicted in SEQ ID NO: 17 and a $V_H$ region as depicted in SEQ ID NO: 18. A particularly preferred binding molecule according to the invention is a monoclonal antibody or antigen-binding fragment thereof comprising a light chain sequence as depicted in SEQ ID NO: 27 and a heavy chain sequence as depicted in SEQ ID NO: 28. A particularly preferred binding molecule according to the invention is a monoclonal antibody consisting of a light chain sequence as depicted in SEQ ID NO: 27 and a heavy chain sequence as depicted in SEQ ID NO: 28. A particularly preferred monoclonal antibody according to the invention is antibody TPP-3583.

The carboxy-terminal portion of each light and heavy chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes often have ADCC activity. Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages. Antibodies according to the invention may be IgG antibodies, specifically IgG1.

Monoclonal Antibodies

Particularly envisaged in accordance with the present invention are monoclonal antibodies and antigen-binding fragments thereof. The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to conventional (polyclonal) antibody preparations that typically include different antibodies directed against different epitopes, monoclonal antibodies contain substantially similar epitope binding sites and are therefore typically directed against the same epitope on an antigen. The term "monoclonal antibody" thus includes recombinant, chimeric, humanized, human, or Human Engineered™ monoclonal antibodies.

Various production methods for generating monoclonal antibodies are known in the art and are described, e.g., in Goding, Monoclonal Antibodies: Principles and Practice, pp. 116-227 (Academic Press, 1996). Suitable techniques include the hybridoma method first described by Kohler et al., Nature, 256: 495 (1975), recombinant DNA methods that involve isolation and sequencing of DNA encoding the monoclonal antibodies, and its subsequent introduction and expression in suitable host cells, and the isolation of antibodies from antibody phage libraries generated using the techniques first described in McCafferty et al., Nature, 348: 552-554 (1990).

Chimeric Antibody

As set forth elsewhere herein, the term "antibody" also includes chimeric antibodies. The phrase "chimeric antibody," as used herein, refers to an antibody containing sequence derived from two different antibodies which typically originate from different species. Specifically, the term refers to an antibody in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies.

Put it differently, the term "chimeric antibody" will be held to mean any antibody wherein the antigen binding site is obtained or derived from a first species and the constant region (which may be intact, partial or modified in accordance with the instant invention) is obtained from a second species. E.g., the antigen binding site may be from a non-human source (e.g., mouse or primate) and the constant region may be human.

Typically, chimeric antibodies may for instance comprise human and murine antibody fragments, generally human constant and mouse variable regions.

Humanized Antibody

As set out previously herein, the present invention in particular relates to (monoclonal) humanized antibodies and antigen-binding fragments thereof derived from the mouse anti-human FXI 1A6 as described in WO 2009/067660 A2.

A "humanized antibody" is generally defined as one that is (I) derived from a non-human source (e.g., a transgenic mouse which bears a heterologous immune system), which antibody is based on a human germline sequence; or (II) CDR-grafted, wherein the CDRs of the variable region are from a non-human origin, while one or more framework regions and/or part of the CDR sequence of the variable region are of human origin and typically the constant region (if any) is of human origin.

The term "humanized antibody" thus includes antibodies in which the variable region in either the heavy or light chain or both of a human antibody is altered by at least partial replacement of one or more CDRs from a non-human antibody of known specificity and, if necessary, by partial framework region replacement and sequence changing. In other words, an antibody in which one or more "donor" CDRs from a non-human antibody (such as mouse, rat, rabbit or non-human primate antibody) of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

The present inventors humanized the mouse 1A6 antibody by determining the 1A6 CDR residues and selecting from a database a human germline sequence with the best overall homology to the murine $V_H$ and $V_L$ sequences as an acceptor human germline framework for grafting $V_H$ and $V_L$ CDRs, respectively, as detailed in Experiment 1. Subsequently, the generated humanized antibodies were subjected to CDR optimization as described in Experiment 2, by exchanging amino acids in the 1A6 for corresponding amino acids in the human germline sequence closest in sequence identity and homology ("germlining"). The present inventors then found that germlined humanized 1A6 antibodies comprising 10, 11, 12, 13 or 14 amino acid substitutions in the CDR sequences, and in particular comprising the CDR sequences disclosed elsewhere herein, exhibit advantageous properties in terms of binding characteristics and biological activity, whereas antibodies with more (TTP-3283, TTP3290) or less amino acid substitutions did not.

For the purposes of the present invention, humanized antibodies that have been CDR optimized ("germlined") are comprised within the term "humanized" antibodies.

The framework regions (FR) within the variable region in a heavy or light chain, or both, of a humanized antibody may comprise solely residues of human origin, in which case these framework regions of the humanized antibody are referred to as "fully human framework regions." A human framework region that comprises a mixture of human and donor framework residues, and is referred to herein as a "partially human framework region." Furthermore, humanized antibodies may comprise residues that are neither found in the recipient antibody nor in the donor antibody. These modifications are made to further refine antibody performance (e.g., to obtain desired affinity).

In general, the humanized antibody will thus comprise substantially all of at least one, and typically two, variable regions, in which all or part of the CDRs correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

Human Antibody

A "human" antibody is hereby defined as one that is not chimeric or "humanized" and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising an amino acid sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

Fragments, Variants and Derivatives

As set out previously herein, the invention encompasses full-length antibodies as well as antigen-binding fragments, variants and derivatives thereof.

Fragments

The term "antibody fragment" refers to a polypeptide derived from a "parent" antibody and retaining its basic structure and function. An antibody fragment is hence preferably capable of binding to its specific antigen, i.e. FXI. Furthermore, an antibody fragment according to the invention comprises the minimum structural requirements of an antibody which allow for antigen binding. This minimum requirement may e.g. be defined by the presence of at least the three light chain CDRs (i.e. CDR1, CDR2 and CDR3 of the $V_L$ region, i.e. $CDR_{L1}$, $CDR_{L2}$ and $CDR_{L3}$) and/or the three heavy chain CDRs (i.e. CDR1, CDR2 and CDR3 of the $V_H$ region, i.e. $CDR_{H1}$, $CDR_{H2}$ and $CDR_{H3}$). Put it differently, the term "antibody fragment" refers to a "functional" or "antigen-binding" polypeptide that retains the antigen-binding site (i.e. the CDRs and optionally (part of) the FR) of a "parent" antibody. Antibody fragments of the invention may be derived from, e.g., monoclonal, recombinant, chimeric, humanized and human "parent" antibodies.

Preferred antigen binding antibody fragments comprise at least one of, preferably all of, a CDR1 of the light chain comprising the sequence KASQSVLYSGDNYLN (SEQ ID NO: 8); a CDR2 of the light chain comprising the sequence AASTLES (SEQ ID NO: 9); a CDR3 of the light chain comprising the sequence QQYNGDPWT (SEQ ID NO: 10); a CDR1 of the heavy chain comprising the sequence TSGMGVG (SEQ ID NO: 11); a CDR2 of the heavy chain comprising the sequence HIDWDDDKYYSPSLKS (SEQ ID NO: 12); and a CDR3 of the heavy comprising the sequence chain IRSSVYAHYYGMDY (SEQ ID NO: 13).

Pursuant with the foregoing, the term "antigen binding antibody fragments" particularly refers to fragments of full-length antibodies, such as (s)dAb, Fv, Fd, Fab, Fab', F(ab')2 or "r IgG" ("half antibody"). Antibody fragments according to the invention may also be modified fragments of antibodies such as scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, "minibodies" exemplified by a structure which is as follows: $(V_H-V_L—CH_3)_2$, $(scFv-CH_3)_2$ or $(scFv-CH_3-scFv)_2$, multibodies such as triabodies or tetrabodies. Furthermore, the definition of the term "antibody fragments" includes constructs comprising said fragments, i.e. monovalent, bivalent and polyvalent/multivalent constructs and, thus, monospecific constructs, specifically binding to only one target antigen, as well as bispecific and polyspecific/multispecific constructs, which specifically bind more than one target antigens, e.g. two, three or more, through distinct antigen binding sites. Moreover, the definition of the term "antibody fragments" includes molecules consisting of only one polypeptide chain as well as molecules consisting of more than one polypeptide chain, which chains can be either identical (homodimers, homotrimers or homo oligomers) or different (heterodimer, heterotrimer or heterooligomer).

Antibody fragments may be produced by recombinant DNA techniques or by enzymatic or chemical cleavage of intact antibodies. Methods for producing such fragments are well-known in the art.

Variants

The term "variant" refers to polypeptides comprising the amino acid sequence of a "parent" binding molecule, such as an antibody or antibody fragment, but containing least one amino acid modification (e.g. a substitution, deletion, or insertion) as compared to the "parent" amino acid sequence, provided that the variant is still capable of (specifically) binding to FXI, in particular human FXI as depicted in SEQ ID NO: 7, and preferably exhibits similar or even improved characteristics as compared to the antibodies TTP-3583 and/or TTP-3577 as assessed in the appended Examples. Variants of the binding molecules of the invention, particularly of antibodies and antibody fragments, are typically prepared by introducing appropriate nucleotide changes into the nucleic acids encoding the antibody or antibody fragment, or by peptide synthesis. Generally, the aforementioned amino acid modifications may be introduced into, or present in, the variable region or the constant region, under the premise that two or more CDRs of the variants cumulatively comprise 10, 11, 12, 13 or 14 amino acid substitutions as compared to the 1A6 CDRs as depicted in SEQ ID NO: 1, 2, 3, 4, 5 and 6. Amino acid modifications can for example be introduced in order to modulate antibody properties like thermodynamic stability, solubility or viscosity which affect pharmaceutical development ("sequence optimization").

As set out previously, amino acid modifications include, for example, deletions from, and/or insertions into, and/or substitutions of, residues within the amino acid sequences of binding molecules described herein, preferably the antibodies or antigen binding antibody fragments. Any combination of deletion, insertion, and substitution can be introduced into the "parent" amino acid sequence in order to arrive at the final product, provided that it possesses the desired characteristics as set out elsewhere herein. The amino acid modifications also may alter post-translational processes of the binding molecules, such as changing the number or position of glycosylation sites.

For example, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs. Amino acid sequence insertions envisaged herein include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. An insertional variant of a binding molecule, in particular an antibody or antibody fragment, of the invention includes a fusion product of an antibody or antibody fragment and an enzyme or another functional polypeptide (e.g., which increases the serum half-life of the binding molecule, e.g. antibody or antibody fragment).

Amino acid substitutions can be introduced into the CDRs of the heavy and/or light chain, in particular the hypervariable regions, or the FR regions in the heavy and/or light chain. Particularly envisaged herein are conservative amino acid substitutions that may be made, for instance, on the basis of similarity in polarity, charge, solubility, hydrophobicity, hydrophilicity, and/or the amphipathic nature of the residues involved.

Preferably, 1, 2, 3, 4, 5, 6, 7, 8, 9, or 10 amino acids may be substituted in the CDRs—provided that the antibody variant cumulatively comprises 10, 11, 12, 13 or 14 amino acid substitutions as compared to the 1A6 CDRs as depicted in SEQ ID NO: 1-6—, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR.

Generally, if amino acids are substituted in one or more or all of the CDRs of the heavy and/or light chain, it is preferred that the then-obtained "variant" sequence is at least 80%, still more preferably at least 90% and most preferably at least 95%, 96%, 97%, 98% or 99% identical to the "parent" CDR sequence. The length of the CDR thus influences the number of possible amino acid substitutions so that the variant sequence is still encompassed by the invention. For example, a CDR having 5 amino acids is preferably 80% identical to its substituted sequence in order to have at least one amino acid substituted. Accordingly, the CDRs of the antibody construct may have different degrees of identity to their substituted sequences, e.g., $CDR_{L1}$ may have 80%, while $CDR_{L3}$ may have 90%.

Preferred substitutions (or replacements) are conservative substitutions. However, any substitution (including non-conservative substitution or one or more from the exemplary substitutions) is envisaged as long as the antibody construct retains its capability to bind FXI and/or its CDRs have an identity to the then substituted sequence of at least 80%, still more preferably at least 90% and most preferably at least 95%, 96%, 97%, 98% or 99%.

As used herein, the term "sequence identity" indicates the extent to which two (nucleotide or amino acid) sequences have identical residues at the same positions in an alignment, and is often expressed as a percentage. Preferably, identity is determined over the entire length of the sequences being compared. Thus, two copies of exactly the same sequence have 100% identity, but sequences that are less highly conserved, and have deletions, additions, or replacements, may have a lower degree of identity. Those skilled in the art will recognize that several algorithms are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), Smith-Waterman (Smith, et al. (1981) J. Mol. Biol. 147:195-197) and ClustalW. Accordingly, the amino acid sequences of SEQ ID Nos: 8, 9, 10, 11, 12 or 13 or the nucleotide sequence of SEQ ID NO: 31 or 32 may serve as "subject sequence" or "reference sequence", while the amino acid sequence or nucleic acid sequence of a polypeptide different therefrom can serve as "query sequence".

The term "sequence homology" indicates the similarity of two (nucleotide or amino acid) sequences attributed to descent from a common ancestor. Homologous biological components (genes, proteins, structures) are called homologs and include orthologs and paralogs.

Preferred binding molecule variants of the invention have a sequence identity or homology in the CDR regions of at least 80%, still more preferably at least 90% and most preferably at least 95%, 96%, 97%, 98%, 99% or almost 100% and exhibits a comparable or improved binding affinity to FXI and/or a comparable or improved biological activity as compared to binding molecules comprising the "parent" CDRs, in particular SEQ ID NO: 8, 9, 10, 11, 12 and 13.

Moreover, the nucleic acid sequence homology or similarity between the nucleotide sequences encoding individual variant CDRs and the nucleotide sequences depicted herein are at least 80%, and more typically with preferably increasing homologies or identities of at least 81%, 82%, 83%, 84%, 85%, 86%, 87%, 88%, 89%, 90%, 91%, 92%, 93%, 94%, 95%, 96%, 97%, 98%, or 99%, and almost 100%.

Besides in the CDRs and FRs, amino acid modifications may also be introduced into the Fc part of a binding molecule, which is preferably a monoclonal antibody or antigen-binding fragment thereof. Such modifications can be used in order to modulate functional properties of the antibody, e.g. interactions with the complement proteins such as C1q and/or Fc receptors on other immune cells, or to modulate serum half-life or antigen-dependent cellular cytotoxicity (ADCC). Thus, mutations for modification of effector functions may be introduced into the Fc domains using routine methods known in the art. Exemplary modifications include Asn297→Ala297 and Asn297→Gln297 resulting in a glycosylation of IgG1, or Lys322→Ala322 and optionally Leu234→Ala234 and Leu235→Ala234 which have been reported to reduce or abolish antibody-derived cell-mediated cytotoxicity (ADCC) and/or complement-derived cytotoxicity (CDC).

Derivatives

The term "binding molecule" also encompasses derivatives. Particularly envisaged herein are derivatives of antibodies or antibody fragments as disclosed elsewhere herein. The term "derivative" generally refers to a binding molecule that has been covalently modified to introduce an additional functionality. Covalent modifications of the binding molecules are generally, but not always, done post-translationally, and can be introduced into the binding molecule by reacting specific amino acid residues of the molecule with an organic derivatizing agent that is capable of reacting with selected side chains or the N- or C-terminal residues. Derivatization of binding molecules can be used to attach therapeutic or diagnostic agents, labels, groups extending the serum half-life of the molecule, or insertion of non-natural amino acids. Possible chemical modifications of the binding molecules of the invention include acylation or acetylation of the N-terminal end or amidation or esterification of the C-terminal end or, alternatively, on both. Chemical modifications such as alkylation (e.g., methylation, propylation, butylation), arylation, and etherification are also envisaged.

Serum Half-life Extension

Examples for means to extend serum half-life of the binding molecules, and in particular antibodies and antigen-binding fragments thereof of the invention includes the attachment of peptides or protein domains binding to other proteins in the human body (such as serum albumin, the immunoglobulin Fc region or the neonatal Fc receptor (FcRn). Further conceivable modifications to extend the serum half-life comprise the extension of an amino group with polypeptide chains of varying length (e.g., XTEN technology or PASylation®), the conjugation of non-proteinaceous polymers, including, but not limited to, various polyols such as polyethylene glycol (PEGylation), polypropylene glycol, polyoxyalkylenes, or copolymers of polyethylene glycol and polypropylene glycol, or of carbohydrates, such as hydroxyethyl starch (e.g., HESylation®) or polysialic acid (e.g., PolyXen® technology). In addition, as is known in the art, amino acid substitutions may be made in various positions within the binding molecule in order to facilitate the addition of said polymers.

Glycosylation

Another type of covalent modification of the binding molecules and in particular antibodies and antigen-binding fragments thereof of the invention comprises altering its glycosylation pattern. As is known in the art, glycosylation patterns can depend on both the amino acid sequence of said molecule (e.g., the presence or absence of particular glycosylation amino acid residues, discussed below), or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of, or substitution by, one or more serine or threonine residues to the starting sequence.

Another means of glycosylation of the binding molecule is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Similarly, deglycosylation (i.e., removal of carbohydrate moieties present on the binding molecule) may be accomplished chemically, e.g. by exposure of the binding molecule to trifluoromethanesulfonic acid, or enzymatically by employing endo- and exo-glycosidases.

Labeling

Further potential covalent modifications of the binding molecules of the invention comprise the addition of one or more labels. The labelling group may be coupled to the binding molecule via spacers of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following exemplary labels include, but are not limited to: isotopic labels, which may be radioactive or heavy isotopes, such as radioisotopes or radionuclides (e.g., $^3H$, $^{14}C$, $^{15}N$, $^{35}S$, $^{89}Zr$, $^{90}Y$, $^{99}Tc$, $^{111}In$, $^{125}I$, $^{131}I$); magnetic labels (e.g., magnetic particles); redox active moieties; optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluorophores or proteinaceous fluorophores; enzymatic groups (e.g. horseradish peroxidase, 1-galactosidase, luciferase, alkaline phosphatase; biotinylated groups; or predetermined polypeptide epitopes recognized by a secondary reporter (e.g., leucine zipper pair sequences, binding sites for secondary antibodies, metal binding domains, epitope tags, etc.)

ADCs

It is also conceivable to add a drug, such as a small molecule compound, to the binding molecules and in particular antibodies or antigen-binding fragments thereof. "Antibody drug conjugates", abbreviated "ADC" are antibodies or antigen-binding fragments thereof linked to drug or agent. The linkage can be established through covalent bonds, or non-covalent interactions such as through electrostatic forces. Various linkers, known in the art, can be employed in order to form the ADC as is known in the art and described herein.

Affinity Tags

The binding molecule, and in particular antibody or antigen-binding fragment thereof, of the invention may also comprise additional domains, which are aid in purification and isolation of the molecule (affinity tags). Non-limiting examples of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. Strep II-tag) and His-tag.

The aforementioned fragments, variants and derivatives may be further adapted in order to improve, e.g., their antigen binding properties. For instance, F(ab')$_2$ or Fab may be engineered to minimize or completely remove the intermolecular disulphide interactions that occur between the $C_{H1}$ and $C_L$ domains. Fv polypeptides may further comprise a polypeptide linker between the $V_H$ and $V_L$ domains that enables the Fv to form the desired structure for antigen binding. The Fab fragment also contains the constant domain of the light chain and the first constant region ($CH_1$) of the heavy chain. Fab fragments differ from Fab' fragments by the addition of a few residues at the carboxy terminus of the heavy chain $CH_1$ region including one or more cysteines from the antibody hinge region. Fab'-SH is the designation herein for Fab' in which the cysteine residue(s) of the constant region bear a free thiol group. F(ab')2 antibody fragments originally were produced as pairs of Fab' fragments which have hinge cysteine residues between them.

The binding molecules of the invention may be provided in "isolated" or "substantially pure" form. "Isolated" or "substantially pure" when used herein means that the binding molecule has been identified, separated and/or recovered from a component of its production environment, such that the "isolated" binding molecule is free or substantially free of other contaminant components from its production environment that might interfere with its therapeutic or diagnostic use. Contaminant components may include enzymes, hormones, and other proteinaceous or non-proteinaceous solutes. "Isolated" binding molecules will thus be prepared by at least one purification step removing or substantially removing these contaminant components. The aforementioned definition is equally applicable to "isolated" polynucleotides, mutatis mutandis.

Specific Binding

The binding molecules of the invention, in particular antibodies and antigen-binding fragments thereof, are advantageously capable of binding to factor XI, in particular human factor XI comprising or consisting of an amino acid sequence as depicted in SEQ ID NO: 7. The terms "binding to" and "recognizing" in all grammatical forms are used interchangeably herein. Preferably, said binding molecules specifically bind to factor XI. The term "specifically binds" generally indicates that a binding molecule, in particular an antibody or antigen-binding fragment thereof as described herein, binds via its antigen binding site more readily to its intended target epitope than to a random, unrelated non-target epitope. Particularly, the term "specifically binds" indicates that the affinity of the binding molecule will be at least about 5 fold, preferably 10 fold, more preferably 25-fold, even more preferably 50-fold, and most preferably 100-fold or more, greater for its target epitope than its affinity for a non-target epitope.

Thus, a binding molecule, and in particular an antibody or antigen-binding fragment thereof, may be considered to specifically bind to its target epitope if it binds said epitope with a dissociation constant ($K_D$) that is less than the antibody's $K_D$ for a non-target epitope. Binding molecules of the invention may also be described in terms of their binding affinity to factor XI, in particular human factor XI. The term "affinity" or "binding affinity" refers to the strength of the binding of an individual epitope with an antigen-binding domain (and in particular the CDRs of the binding molecule). The affinity of the binding of a given binding molecule to its specific epitope is often determined by measurement of the equilibrium association constant (ka) and equilibrium dissociation constant (kd) and calculating the quotient of kd to ka ($K_D$=kd/ka). Binding affinities may be readily determined using conventional techniques, such as by equilibrium dialysis; by using the BIAcore 2000 instrument; by radioimmunoassay using radiolabeled target antigen; or by another method known to the skilled artisan. The affinity data may be analyzed, for example, by the method described in Kaufman R J and Sharp P A. (1982) J Mol Biol. 159:601-621. Preferred binding affinities of the inventive binding molecules include those with a dissociation constant or $K_D$ less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Cross-reactivity

The term "specifically binds" however does not exclude that the binding molecules (specifically) binding to human factor XI cross-reacts with a factor XI protein from a different species. Accordingly, binding molecules of the invention may also be capable of binding to FXI from other mammalian species, preferably non-human primate species as exemplified elsewhere herein.

"Cross-species" binding or recognition means binding of a binding domain described herein to the same target antigen in humans and non-human species. Thus, "cross-species specificity" is to be understood as an interspecies reactivity to Factor XI expressed in different species, but not to an antigen other than Factor XI. E.g., a binding domain which binds to human factor XI, in particular to the A3 domain comprising amino acids 200 to 283 of the amino acid sequence shown in SEQ ID NO:7 may also bind to non-human primate Factor XI, and in particular to a region corresponding to amino acids 200 to 283 of the amino acid sequence shown in SEQ ID NO: 7.

Biological Activity

The binding molecules provided herein are envisaged to be biologically active, i.e. to bind to Factor XI and/or Factor XIa and block its respective biological functions. Specifically, "biologically active" binding molecules according to the invention block the conversion of Factor XI to its active form (Factor XIa) and/or block binding of downstream coagulation Factor IX to Factor XIa, preferably resulting in a complete or partial inhibition of Factor XI and/or Factor XIa activity. Binding of the biologically active binding molecules to their target Factor XI and/or Factor XIa is thus envisaged to result in an anticoaguatory activity. Put it differently, it is envisaged that the binding molecules according to the invention exert their beneficial function via a) binding to Factor XI, thereby blocking its conversion into its active form Factor XIa, and/or b) binding to Factor XIa, thereby blocking its binding to and activating of downstream coagulation Factor IX. Binding molecules of the invention thereby preferably interrupt the "FXI branch" of the coagulation cascade and thereby prevent thrombosis, advantageously without impairing normal hemostasis.

The anticoagulatory activity of a binding molecule can be determined in vitro as described in the appended Experiments. Briefly, the activated partial thromboplastin time (aPTT) is determined in the presence of varying concentrations of said binding molecule or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects a 1.5 fold prolongation of the aPTT is determined.

It is envisaged that concentrations of the binding molecules of the present invention lead to a 1.5 fold prolongation of the aPTT at a concentration of 0.03 µM or less, or 0.015 µM or less, or 0.01 µM or less.

Advantageously, binding molecules and in particular monoclonal antibodies and antigen binding fragments thereof according to the invention exhibit the abovementioned biological properties and are therefore promising new agents for inhibition of thrombosis. Because the binding molecules are particularly envisaged to specifically bind to Factor XI, it is envisaged that they do not, or do not severely, compromise hemostasis and thereby preferably do not increase the risk of bleeding.

Polynucleotide

The invention further provides a polynucleotide/nucleic acid molecule encoding a binding molecule or a $V_H$ or a $V_L$ domain of the invention.

The term "polynucleotide" as used herein comprises polyribonucleotides and polydeoxyribonucleotides, e.g. modified or unmodified RNA or DNA, each in single-stranded and/or double-stranded form, linear or circular, or mixtures thereof, including hybrid molecules. A polynucleotide may comprise a conventional phosphodiester bond or a non-conventional bond (e.g., an amide bond, such as found in peptide nucleic acids (PNA)). The polynucleotides of the invention may also contain one or more modified bases, such as, for example, tritylated bases and unusual bases such as inosine. Other modifications, including chemical, enzymatic, or metabolic modifications, are also conceivable, as long as a binding molecule of the invention can be expressed from the polynucleotide. The polynucleotide may be provided in isolated form as defined elsewhere herein. A polynucleotide may include regulatory sequences such as transcription control elements (including promoters, enhancers, operators, repressors, and transcription termination signals), ribosome binding site, introns, or the like.

In accordance, the present invention provides a polynucleotide comprising, or consisting of a nucleic acid encoding an immunoglobulin heavy chain region ($V_H$ region), where at least one of the CDRs of the $V_H$ region has an amino acid sequence that is at least about 80%, about 85%, about 90%, about 95%, about 96%, about 97%, about 98%, about 99%, or identical to any one of SEQ ID NO: 11, 12, 13, 15 or 16, with SEQ ID NO: 11-13 being preferred. Further, the present invention includes a polynucleotide comprising, or consisting of a nucleic acid encoding a $V_H$ region that has an amino acid sequence that is at least about 80%, about 85%, about 90%, about 91%, about 92%, about 93%, about 94%, about 95%, about 96%, about 97%, about 98%, about 99%, or 100% identical to a reference $V_H$ region amino acid sequence selected from the group consisting of SEQ ID NO:18 and 20, with SEQ ID NO: 18 being preferred. A binding molecule comprising the encoded CDRs or $V_H$ domains is envisaged to be capable of binding to FXI and preferably exhibit the desired biological activities as described elsewhere herein.

Further, the present invention provides a polynucleotide comprising, or consisting of a nucleic acid encoding an immunoglobulin light chain domain ($V_L$ region), where at least one of the CDRs of the $V_L$ region has an amino acid sequence that is at least about 80%, about 85%, about 90%, about 95%, about 96%, about 97%, about 98%, about 99%, or identical to any one of SEQ ID NOS: 8, 9, 10 or 14, with SEQ ID Nos. 8-10 being preferred. Moreover, the present invention includes a polynucleotide comprising, or consisting of a nucleic acid encoding a $V_L$ region that has an amino acid sequence that is at least about 80%, about 85%, about 90%, about 91%, about 92%, about 93%, about 94%, about 95%, about 96%, about 97%, about 98%, about 99%, or 100% identical to a reference $V_L$ region amino acid sequence selected from the group consisting of SEQ ID NO:17 or 19, with SEQ ID NO: 17 being preferred. A binding molecule comprising the encoded CDRs or $V_L$ regions is envisaged to be capable of binding to FXI and preferably exhibit the desired biological activities as described elsewhere herein.

Further, the present invention provides an isolated polynucleotide comprising, or consisting of a nucleic acid that is at least about 80%, about 85%, about 90%, about 91%, about 92%, about 93%, about 94%, about 95%, about 96%, about 97%, about 98%, about 99%, or 100% identical to a reference polynucleotide sequence selected from the group consisting of SEQ ID NO: 31, 32, 33 and 34.

The polynucleotides described above may or may not comprise additional nucleotide sequences, encoding, e.g., a signal peptide to direct secretion of the encoded polypeptide, antibody constant regions as described herein, or other heterologous polypeptides as described herein. Such polynucleotides may thus encode fusion polypeptides, fragments, variants and other derivatives of the binding molecules described herein.

Also, the present invention includes compositions comprising one or more of the polynucleotides described above. Also provided herein are compositions comprising a first polynucleotide and second polynucleotide wherein said first polynucleotide encodes a $V_H$ region as described herein and wherein said second polynucleotide encodes a $V_L$ region as described herein, specifically a composition which comprises, or consists of a $V_H$ region selected from the group consisting of SEQ ID NO: 18 and 20 (with SEQ ID NO: 18 being preferred), and/or a $V_L$ region selected from the group consisting of SEQ ID NO:17 and 19 (with SEQ ID NO: 17 being preferred).

Production of Polynucleotides

Polynucleotides of the invention may be produced by routine methods known in the art. For example, if the nucleotide sequence of the binding molecule is known, a polynucleotide encoding the binding molecule may be assembled from chemically synthesized oligonucleotides, annealing and ligating of those oligonucleotides, and then amplification of the ligated oligonucleotides by PCR. A polynucleotide encoding a binding molecule may be obtained from a suitable source (e.g., a cDNA library, or a nucleic acid such as a poly(A)+ mRNA isolated from any tissue or cells expressing the binding molecule such as hybridoma cells) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the binding molecule.

Once the nucleotide sequence and corresponding amino acid sequence of the binding molecule is determined, its nucleotide sequence may be modified using methods well known in the art for the manipulation of nucleotide sequences, e.g., recombinant DNA techniques, site directed mutagenesis, PCR, etc., thereby introducing one or more nucleotide substitutions, additions or deletions into the polynucleotide sequence (see, for example, the techniques described in J. Sambrook et al., Molecular Cloning: A Laboratory Manual (4th edition), Cold Spring Harbor Laboratory, Cold Spring Harbor Laboratory Press, New York (2012)) to generate non-naturally occurring fragments, variants or derivatives of the binding molecule, and in particular the monoclonal anti-FXI antibody described herein (e.g., an immunoglobulin heavy chain region or light chain region).

Vectors

Further provided herein is a vector comprising the polynucleotide as described herein. Said polynucleotide encodes a binding molecule of the invention, in particular a monocional antibody or antigen binding fragment thereof. A "vector" is a nucleic acid molecule used as a vehicle to transfer (foreign) genetic material into a host cell where it can for instance be replicated and/or expressed.

The term "vector" encompasses, without limitation, plasmids, viral vectors (including retroviral vectors, lentiviral vectors, adenoviral vectors, vaccinia virus vectors, polyoma virus vectors, and adenovirus-associated vectors (AAV)), phages, phagemids, cosmids and artificial chromosomes (including BACs and YACs). The vector itself is generally a nucleotide sequence, commonly a DNA sequence that comprises an insert (transgene) and a larger sequence that serves as the "backbone" of the vector. Engineered vectors typically comprise an origin for autonomous replication in the host cells (if stable expression of the polynucleotide is desired), selection markers, and restriction enzyme cleavage sites (e.g. a multiple cloning site, MCS). Vector may additionally comprise promoters, genetic markers, reporter genes, targeting sequences, and/or protein purification tags. Vectors called expression vectors (expression constructs) are specifically designed for the expression of the transgene in the target cell, and generally have control sequences.

Large numbers of suitable vectors are known to those of skilled in the art and many are commercially available. Examples of suitable vectors are provided in J. Sambrook et al., Molecular Cloning: A Laboratory Manual (4th edition), Cold Spring Harbor Laboratory, Cold Spring Harbor Laboratory Press, New York (2012).

Targeting Vectors

Targeting vectors can be used to integrate a polynucleotide into the host cell's chromosome (such as described by J. Sambrook et al., Molecular Cloning: A Laboratory Manual (4th edition), Cold Spring Harbor Laboratory, Cold Spring Harbor Laboratory Press, New York (2012)). Briefly, suitable means include homologous recombination or use of a hybrid recombinase that specifically targets sequences at the integration sites. Targeting vectors are typically circular and linearized before used for homologous recombination. As an alternative, the foreign polynucleotides may be DNA fragments joined by fusion PCR or synthetically constructed DNA fragments which are then recombined into the host cell. It is also possible to use heterologous recombination which results in random or non-targeted integration.

Production

Expression Vectors

"Expression vectors" or "expression constructs" can be used for the transcription of heterologous polynucleotide sequences, for instance those encoding the binding molecules of the invention, and translation of their mRNA in a suitable host cell. This process is also referred to as "expression" of the binding molecules of the invention herein. Besides an origin of replication, selection markers, and restriction enzyme cleavage sites, expression vectors typically includes one or more regulatory sequences operably linked to the heterologous polynucleotide to be expressed.

The term "regulatory sequence" refers to a nucleic acid sequence necessary for the expression of an operably linked coding sequence of a (heterologous) polynucleotide in a particular host organism and thus include transcriptional and translational regulatory sequences. Typically, regulatory sequences required for expression of heterologous polynucleotide sequences in prokaryotes include a promoter(s), optionally operator sequence(s), and ribosome binding site(s). In eukaryotes, promoters, polyadenylation signals, enhancers and optionally splice signals are typically required. Moreover, specific initiation and secretory signals also may be introduced into the vector in order to allow for secretion of the polypeptide of interest into the culture medium.

A nucleic acid is "operably linked" when it is placed into a functional relationship with another nucleic acid sequence, in particular on the same polynucleotide molecule. For example, a promoter is operably linked with a coding sequence of a heterologous gene when it is capable of effecting the expression of that coding sequence. The promoter is typically placed upstream of the gene encoding the polypeptide of interest and regulates the expression of the gene.

Exemplary regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof (see U.S. Pat. No. 5,168,062 by Stinski; U.S. Pat. No. 4,510,245 by Bell et al.; U.S. Pat. No. 4,968,615 by Schaffner et al.). As set out before, the expression vectors may also include origins of replication and selectable markers.

As mentioned previously, vectors of the invention may further comprise one or more selection markers. Suitable selection markers for use with eukaryotic host cells include, without limitation, the herpes simplex virus thymidine kinase (tk), hypoxanthine-guanine phosphoribosyltransferase (hgprt), and adenine phosphoribosyltransferase (aprt) genes. Other genes include dhfr (methotrexate resistance), gpt (mycophenolic acid resistance) neo (G-418 resistance) and hygro (hygromycin reistance). Vector amplification can be used to increase expression levels. In general, the selection marker gene can either be directly linked to the polynucleotide sequences to be expressed, or introduced into the same host cell by cotransformation.

In view of the above, the present invention thus further provides one or more of the polynucleotide sequences described herein inserted into a vector. The invention thus, particularly, provides replicable vectors comprising a nucleotide sequence encoding a binding molecule of the invention, or a heavy or light chain thereof, or a heavy or light chain variable domain, operably linked to a promoter. Such vectors may include the nucleotide sequence encoding the constant region of the binding molecule and the variable domain of the binding molecule may be cloned into such a vector for expression of the entire heavy or light chain.

Host Cell

In general, a variety of host cells may be employed to express the binding molecule of the invention from an expression vector. As used herein, a "host cell" refers to a cell which can be or has/have been recipients of polynucleotides or vectors or encoding the binding molecule of the present invention. Specifically, a host cell may further be capable of expressing and optionally secreting said binding molecule. In descriptions of processes for obtaining binding molecules from host cells, the terms "cell" and "cell culture" are used interchangeably to denote the source of a binding molecule unless it is clearly specified otherwise. The term "host cell" also includes "host cell lines".

In general, the term includes prokaryotic or eukaryotic cells, and also includes without limitation bacteria, yeast cells, fungi cells, plant cells, and animal cells such as insect cells and mammalian cells, e.g., murine, rat, macaque or human cells.

Polynucleotides and/or vectors of the invention can be introduced into the host cells using routine methods known in the art, e.g. by transfection, transformation, or the like.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside. Exemplary techniques for transfecting eukaryotic host cells include lipid vesicle mediated uptake, heat shock mediated uptake, calcium phosphate mediated transfection (calcium phosphate/DNA co-precipitation), microinjection and electroporation.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethylene glycol mediated uptake.

In view of the above, the present invention thus further provides host cells comprising at least one polynucleotide sequence and/or vector as described herein.

For expression of the binding molecule of the invention, a host cell may be chosen that modulates the expression of the inserted polynucleotide sequences, and/or modifies and processes the gene product (i.e. RNA and/or protein) as desired. Such modifications (e.g., glycosylation) and processing (e.g., cleavage) of gene products may be important for the function of the binding molecule. Different host cells have characteristic and specific mechanisms for the post-translational processing and modification of gene products. Appropriate cell lines or host systems can be chosen to ensure the correct modification and processing of the product. To this end, eukaryotic host cells that possess the cellular machinery for proper processing of the primary transcript, glycosylation, and phosphorylation of the gene product may be used.

Exemplary mammalian host cells that can be used for expressing the binding molecules provided herein include Chinese Hamster Ovary (CHO cells) including DHFR minus CHO cells such as DG44 and DUXBI 1 and as described in U.S. Pat. No. 4,634,665 (e.g. used with a DHFR selectable marker, e.g., as described in U.S. Pat. No. 5,179,017), NSO, COS (a derivative of CVI with SV40 T antigen), HEK293 (human kidney), and SP2 (mouse myeloma) cells. Other exemplary host cell lines include, but are not limited to, HELA (human cervical carcinoma), CVI (monkey kidney line), VERY, BHK (baby hamster kidney), MDCK, 293, WI38, R1610 (Chinese hamster fibroblast) BALBC/3T3 (mouse fibroblast), HAK (hamster kidney line), P3x63-Ag3.653 (mouse myeloma), BFA-IcIBPT (bovine endothelial cells), and RAJI (human lymphocyte). Host cell lines are typically available from commercial services, the American Tissue Culture Collection or from published literature.

Non-mammalian cells such as bacterial, yeast, insect or plant cells are also readily available and can in principle be used for expression of the binding molecules of the invention. Exemplary bacterial host cells include enterobacteriaceae, such *Escherichia coli, Salmonella*; Bacillaceae, such as *Bacillus subtilis; Pneumococcus; Streptococcus*, and *Haemophilus* influenza.

Other host cells include yeast cells, such as *Saccharomyces cerevisiae*, and *Pichia pastoris*. Insect cells include, without limitation, *Spodoptera frugiperda* cells.

In accordance with the foregoing, conceivable expressions systems (i.e. host cells comprising an expression vector as described above) include microorganisms such as bacteria (e.g., *E. coli, B. subtilis*) transformed with recombinant bacteriophage DNA, plasmid DNA or cosmid DNA expression vectors; yeast (e.g., *Saccharomyces, Pichia*) transformed with recombinant yeast expression vectors; insect cell systems infected with recombinant virus expression vectors (e.g., baculovirus); plant cell systems infected with recombinant virus expression vectors (e.g., cauliflower mosaic virus, CaMV; tobacco mosaic virus, TMV) or transformed with recombinant plasmid expression vectors (e.g., Ti plasmid); or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For expression of the binding molecules of the invention, eukaryotic cells are particularly envisaged. Accordingly, CHO cells comprising a eukaryotic vector with a polynucleotide sequence encoding the binding molecule of the invention (which may for instance be operably linked to the major immediate-early promoter (MIEP) of human cytomegalovirus (CMV)) are useful expression systems for producing the binding molecules of the invention.

Cultivation

The host cells harboring the expression vector are grown under conditions appropriate to the production of the binding molecules described herein, in particular light chains and heavy chains as described elsewhere herein, and assayed for heavy and/or light chain protein synthesis. Thus, the invention includes host cells containing a polynucleotide encoding a binding molecule of the invention, or a heavy or light chain thereof, operably linked to a promoter. For the expression of double-chained antibodies, vectors encoding both the heavy and light chains may be co-expressed in the host cell for expression of the entire molecule.

Purification

Once a binding molecule of the invention has been recombinantly expressed, it may be purified by any purification method known in the art, for example, by chromatography (e.g., ion exchange chromatography (e.g. hydroxylapatite chromatography), affinity chromatography, particularly Protein A, Protein G or lectin affinity chromatography, sizing column chromatography), centrifugation, differential solubility, hydrophobic interaction chromatography, or by any other standard technique for the purification of proteins. The skilled person will readily be able to select a suitable purification method based on the individual characteristics of the binding molecule to be recovered.

In view of the above, the present invention thus also provides a process for the production of a binding molecule of the invention, comprising culturing a host cell as defined herein under conditions allowing the expression of the binding molecule and optionally recovering the produced binding molecule from the culture.

Pharmaceutical Composition

The present invention further provides a pharmaceutical composition comprising a binding molecule, nucleic acid, vector and/or host cell of the invention, and optionally one or more pharmaceutically acceptable excipient(s). A preferred pharmaceutical composition comprises an antibody of the invention and optionally one or more pharmaceutically acceptable excipient(s).

In one aspect, the invention thus relates to a pharmaceutical composition comprising, as an active agent, a binding molecule as described herein, in particular an anti-FXI antibody or an antigen-binding fragment thereof. Accordingly, the use of the said binding molecules for the manufacture of a pharmaceutical composition is also envisaged herein. The term "pharmaceutical composition" particularly refers to a composition suitable for administering to a human. However, compositions suitable for administration to non-human animals are also encompassed by the term.

The pharmaceutical composition and its components (i.e. active agents and optionally excipients) are preferably pharmaceutically acceptable, i.e. capable of eliciting the desired therapeutic effect without causing any undesirable local or systemic effects in the recipient. Pharmaceutically acceptable compositions of the invention may in particular be sterile and/or pharmaceutically inert. Specifically, the term "pharmaceutically acceptable" may mean approved by a regulatory agency or other generally recognized pharmacopoeia for use in animals, and more particularly in humans.

The binding molecule described herein is preferably present in the pharmaceutical composition in a therapeutically effective amount. By "therapeutically effective amount" is meant an amount of the binding molecule that elicits the desired therapeutic effect. Therapeutic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred.

As set out previously, the pharmaceutical composition may optionally comprise one or more excipients and/or additional active agents.

Antibodies and fragments thereof are generally administered parenterally, and particularly intravenously (injection or infusion) or subcutaneously. Compositions for parenteral administration include sterile aqueous or non-aqueous solutions, suspensions and emulsions. Non-aqueous solvents include without limitation, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media such as without limitation phosphate buffered saline solution. Parenteral vehicles further include sodium chloride solution, Ringer's dextrose, dextrose and sodium chloride, lactated Ringer's, or fixed oils. Other suitable pharmaceutical carriers, diluents and/or excipients are well known in the art. The binding molecule, such as an antibody or antibody fragment thereof, according to the present invention may be combined with a pharmaceutically acceptable carrier, diluent and/or excipient such as those discussed above to form a pharmaceutical composition. The pharmaceutical compositions may comprise the binding molecule of the present invention in an aqueous carrier that comprises a buffering agent selected from the group consisting of a histidine buffer, acetic acid buffer, citric acid buffer, and a histidine/HCl buffer. Additional buffers and formulation information is available to one of skill in the art, for example in Wang W et al., J. Pharmaceutical Sci. 2007 Jan. (1):1-26. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. In one embodiment, the pharmaceutical composition comprises the binding molecule in lyophilized form and preferably is reconstituted in solution or suspension prior to administration. In another embodiment, the pharmaceutical composition comprises the binding molecule and is in liquid form.

After pharmaceutical compositions of the invention and optionally a suitable excipient have been prepared, they can be placed in an appropriate container and labeled for treatment of an indicated condition. Such labeling would for instance include amount, frequency and method of administration.

Additional Active Agents

The present invention further provides medicaments or pharmaceutical compositions comprising an inventive compound and one or more further active ingredients, especially for treatment and/or prophylaxis of the disorders mentioned herein. Preferred examples of active ingredients suitable for combinations include:

lipid-lowering substances, especially HMG-CoA (3-hydroxy-3-methylglutaryl-coenzyme A) reductase inhibitors, including without limitation lovastatin (Mevacor), simvastatin (Zocor), pravastatin (Pravachol), fluvastatin (Lescol) and atorvastatin (Lipitor);

coronary therapeutics/vasodilatators, especially ACE (angiotensin converting enzyme) inhibitors, including without limitation captopril, lisinopril, enalapril, ramipril, cilazapril, benazepril, fosinopril, quinapril and perindopril, or AII (angiotensin II) receptor antagonists, including without limitation embusartan, losartan, valsartan, irbesartan, candesartan, eprosartan and temisartan, or adrenoceptor antagonists, including without limitation carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, including without limitation prazosine, bunazosine, doxazosine and terazosine, or diuretics, including without limitation hydrochlorothiazide, furosemide, bumetanide, piretanide, torasemide, amiloride and dihydralazine, or calcium channel blockers, including without limitation verapamil and diltiazem, or dihydropyridine derivatives, including without limitation nifedipin (Adalat) and nitrendipine (Bayotensin), or nitro preparations, including without limitation isosorbide 5-mononitrate, isosorbide dinitrate and glycerol trinitrate, or substances causing an increase in cyclic guanosine monophosphate (cGMP), including without limitation stimulators of soluble guanylate cyclase, including without limitation dociguat;

plasminogen activators (thrombolytics/fibrinolytics) and compounds which promote thrombolysis/fibrinolysis including without limitation inhibitors of the plasminogen activator inhibitor (PAI inhibitors) or inhibitors of the thrombin-activated fibrinolysis inhibitor (TAFI inhibitors), including without limitation tissue plasminogen activator (t-PA), streptokinase, reteplase and urokinase;

anticoagulatory substances (anticoagulants), including without limitation heparin (UFH), low-molecular-weight heparins (LMW), including without limitation tinzaparin, certoparin, pamaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI), including without limitation Pradaxa (dabigatran), atecegatran (AZD-0837), DP-4088, SSR-182289A, argatroban, bivalirudin and tanogitran (BIBT-986 and prodrug BIBT-1011), hirudin;

direct factor Xa inhibitors including without limitation, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, platelet aggregation-inhibiting substances (platelet aggregation inhibitors, thrombocyte aggregation inhibitors), including without limitation acetylsalicylic acid (for example Aspirin), ticlopidine (Ticlid), clopidogrel (Plavix), prasugrel, ticagrelor, cangrelor, elinogrel, vorapaxar;

fibrinogen receptor antagonists (glycoprotein-IIb/IIIa antagonists), including without limitation abciximab, eptifibatide, tirofiban, lamifiban, lefradafiban and fradafiban;

antiarrhythmics;

various antibiotics or antifungal medicaments, either as calculated therapy (prior to the presence of the microbial diagnosis) or as specific therapy;

vasopressors, including without limitation norepinephrine, dopamine and vasopressin;

inotropic therapy, including without limitation dobutamine;

recombinant human activated protein C, for example Xigris;

blood products, including without limitation erythrocyte concentrates, thrombocyte concentrates, erythropietin and fresh frozen plasma;

inhibitors of platelet adhesion like GPVI and/or GPIb antagonists including without limitation Revacept or Caplacizumab;

inhibitors of the VEGF and/or PDGF dependent signal transduction pathways including without limitation Aflibercept, Ranibizumab, Bevacizumab, KH-902, Pegaptanib, Ramucirumab, Squalamin oder Bevasiranib, Apatinib, Axitinib, Brivanib, Cediranib, Dovitinib, Lenvatinib, Linifanib, Motesanib, Pazopanib, Regorafenib, Sorafenib, Sunitinib, Tivozanib, Vandetanib, Vatalanib, Vargatef or E-10030;

inhibitors of the Angiopoietin-Tie signal transduction pathway including without limitation AMG386;

inhibitors of the Tie2 receptor tyrosine kinase activity;

inhibitors of the Integrine dependent signal transduction pathways including without limitation Volociximab, Cilengitid or ALG1001;

inhibitors of the PI3Kinase-AKT-mTor dependent signal transduction including without limitation XL-147, Perifosin, MK2206, Sirolimus, Temsirolimus or Everolimus;

Corticosteroids including without limitation hydrocortisone, fludrocortisone, Anecortave, Betamethason, Dexamethason, Triamcinolon, Fluocinolon or Fluocinolonacetonid;

inhibitors of the ALK1-Smad1/5 dependent signal transduction pathway including without limitation ACE041;

inhibitors of Cyclooxygeneases including without limitation Bromfenac or Nepafenac;

inhibitors of the Kallikrein-Kinin system including without limitation Safotibant or Ecallantid;

inhibitors of the Sphingosin-1-phosphat dependent signal transduction pathways including without limitation Sonepcizumab;

inhibitors of the Complement C5a receptor including without limitation Eculizumab;

inhibitors of the 5HT1a receptor including without limitation Tandospiron;

inhibitors of the Raf-Mek-Erk dependent signal transduction pathway, inhibitors of the MAPK signal transduction pathway; inhibitors of the FGF signal transduction pathway, inhibitors of endothelial cell proliferation; and compounds which are able to induce apoptosis; or Photodynamic therapies, consisting of an active substance and the exposure to light, whereas the active substance is for example Verteporfin.

"Combinations" for the purpose of the invention mean not only dosage forms which contain all the components (so-called fixed combinations) and combination packs which contain the components separate from one another, but also components which are administered simultaneously or sequentially, provided that they are used for prophylaxis and/or treatment of the same disease. It is likewise possible to combine two or more active ingredients with one another, meaning that they are thus each in two-component or multicomponent combinations.

Administration

A variety of routes are applicable for administration of the pharmaceutical composition according to the present invention. Typically, administration will be accomplished parentally. Methods of parenteral delivery include topical, intra-arterial, intramuscular, subcutaneous, intramedullary, intrathecal, intraventricular, intravenous, intraperitoneal, intrauterine, intravaginal, sublingual or intranasal administration.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Exemplary lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art. Further details on techniques for formulation and administration may be found in the 22nd edition of Remington's Pharmaceutical Sciences (Ed. Maack Publishing Co, Easton, Pa., 2012).

Treatment

The term "treatment" in all its grammatical forms includes therapeutic or prophylactic treatment of the diseases described herein. A "therapeutic or prophylactic treatment" comprises prophylactic treatments aimed at the complete prevention of clinical and/or pathological manifestations or therapeutic treatment aimed at amelioration or remission of clinical and/or pathological manifestations. The term "treatment" thus also includes the amelioration or prevention of the described diseases.

The terms "subject" or "individual" or "animal" or "patient" are used interchangeably herein to refer to any subject, particularly a mammalian subject, for whom therapy is desired.

Mammalian subjects include humans, non-human primates, dogs, cats, guinea pigs, rabbits, rats, mice, horses, cattle, cows, and the like.

Dosage

The exact dosage of the binding molecule, polynucleotide, vector or host cell will be ascertainable by one skilled in the art using known techniques. Suitable dosages provide sufficient amounts of the binding molecule and are preferably therapeutically effective, i.e. elicit the desired therapeutic effect.

As is known in the art, adjustments for purpose of the treatment (e.g. remission maintenance vs. acute flare of disease), route, time and frequency of administration, time and frequency of administration formulation, age, body weight, general health, sex, diet, severity of the disease state, drug combination(s), reaction sensitivities, and tolerance/response to therapy may be necessary. Suitable dosage ranges can be determined using data obtained from cell culture assays and animal studies and preferably include the $ED_{50}$. Typically, dosage amounts may vary from 0.1 to 100000 micrograms, up to a total dose of about 2 g, depending upon the route of administration. Exemplary dosages of the binding molecule are in the range from about 0.01 mg/kg to about 10 mg/kg, from about 0.1 mg/kg to about 10 mg/kg, from about 1 mg/kg to about 10 mg/kg, from about 1 mg/kg to about 5 mg/kg, from about 0.01 mg/kg to about 1 mg/kg, or from about 0.1 mg/kg to about 1 mg/kg. Guidance as to particular dosages and methods of delivery is provided in the literature. It is recognized that treatment may require a single administration of a therapeutically effective dose or multiple administrations of a therapeutically effective dose of the binding molecule, polynucleotide, vector or host cell of the invention. E.g., some pharmaceutical compositions might be administered every 3 to 4 days, every week, or once every two weeks, or once within a month depending on formulation, half-life and clearance rate of the particular formulation.

Kit

The invention further relates to pharmaceutical packs and kits comprising one or more containers or vials filled with one or more of the active agents of the aforementioned pharmaceutical compositions of the invention. Thus, also provided herein is a kit comprising a binding molecule, a polynucleotide, a vector, a host cell and/or the pharmaceutical composition as described herein. The aforementioned kits described herein may be used for treatment of the diseases set out elsewhere herein, or for other purposes.

Associated with the aforementioned container(s) can be a notice in the form prescribed by a governmental agency regulating the manufacture, use or sale of pharmaceuticals or biological products, reflecting approval by the agency of the manufacture, use or sale of the product for human administration.

The kit may comprise one or more active agents (optionally formulated as a pharmaceutical compositions with one or more excipients). Suitable active agents have previously been listed in the context of the pharmaceutical composition and are also conceivable as parts of the inventive kit. The additional active agent can be administered simultaneously or sequentially with respect to the binding molecule, nucleic acid sequence, vector, host cell and/or the pharmaceutical composition to the patient. The present invention further encompasses the administration of the active agents via different routes, e.g. orally and intravenously.

Further envisaged herein are kits comprising polynucleotide sequences encoding the binding molecules of the invention. Said polynucleotides are typically provided in a vector, such as a plasmid, suitable for transfection into and expression by a host cell. Such vectors and host cells are described elsewhere herein.

Therapeutic Use

The present invention further provides binding molecules of this invention, preferably antibodies and antigen-binding fragments thereof, for use as medicaments for the treatment and/or prophylaxis of diseases in humans and/or animals.

The present invention further provides binding molecules of the invention, preferably antibodies and antigen-binding fragments thereof, for use in the treatment and/or prophylaxis of disorders, in particular cardiovascular disorders, preferably thrombotic or thromboembolic disorders and/or thrombotic or thromboembolic complications.

Factor XIa (FXIa) is an important enzyme in the context of coagulation, which can be activated both by thrombin and factor XIIa (FXIIa), and is therefore involved in two essential processes of coagulation: It is a central component of the transition from initiation to amplification and propagation of coagulation: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated, leading to strong thrombus growth and stabilizing the thrombus.

Moreover, factor XIa is an important component for the intrinsic initiation of coagulation: In addition to the stimulation via tissue factor (TF), the coagulation system can be activated also particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa (FXIIA) which subsequently activates FXI, attached to cell surfaces, to FXIa. This leads to further activation of the coagulation cascade as described above.

In contrast, thrombin generation in the initiation phase remains uninfluenced via TF/factor VIIa and factor X activation and finally thrombin formation, the physiological reaction on vascular injuries. This could explain why no prolongations of bleeding times were found in FXIa knockout mice, as in rabbits and other species, with administration of FXIa inhibitor. This low bleeding tendency caused by the substance is of great advantage for use in humans, particularly in patients with increased risk of bleeding.

Accordingly, the binding molecules of the invention, preferably antibodies and antigen-binding fragments thereof, are for use in the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the binding molecules of the invention, preferably antibodies and antigen-binding fragments thereof, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The binding molecules of the invention, preferably antibodies and antigen-binding fragments thereof, are therefore for use in the prophylaxis of thromboses in the context of surgical interventions for example in patients suffering from cancer or patients receiving an orthopaedic surgery, like hip or knee replacement. The binding molecules of the invention, preferably antibodies and antigen-binding fragments thereof, are therefore also for use in the prophylaxis of thromboses in patients having an activated coagulation system, for example in the stimulation situations described.

The binding molecules of the invention, preferably antibodies and antigen-binding fragments thereof, are therefore also for use in the treatment and/or prophylaxis of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves.

In addition, the binding molecules of the invention, preferably antibodies and antigen-binding fragments thereof, are for use in the treatment and/or prophylaxis of disseminated intravascular coagulation (DIC) which may occur in connection with sepsis inter alia, but also owing to surgical interventions, neoplastic disorders, burns or other injuries and may lead to severe organ damage through microthromboses.

Thromboembolic complications furthermore occur in microangiopathic haemolytical anaemias and by the blood coming into contact with foreign surfaces in the context of extracorporeal circulation such as, for example, haemodialysis, ECMO ("extracorporeal membrane oxygenation"), LVAD ("left ventricular assist device") and similar methods, AV fistulas, vascular and heart valve prostheses.

Moreover, the binding molecules of the invention, preferably antibodies and antigen-binding fragments thereof, are for use in the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the binding molecules of the invention, preferably antibodies and antigen-binding fragments thereof, can be used for the prophylaxis and/or treatment of thrombotic and/or thromboembolic complications, such as, for example, venous thromboembolisms in cancer patients, in particular those undergoing major surgical interventions or chemo- or radiotherapy.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

In addition, the binding molecules of the invention, preferably antibodies and antigen-binding fragments thereof, are also for use in the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure. In the course of an infection, there may be a generalized activation of the coagulation system (disseminated intravascular coagulation or consumption coagulopathy, herein below referred to as "DIC") with microthrombosis in various organs and secondary haemorrhagic complications. Moreover, there may be endothelial damage with increased permeability of the vessels and diffusion of fluid and proteins into the extravasal space. As the infection progresses, there may be failure of an organ (for example kidney failure, liver failure, respiratory failure, central-nervous deficits and cardiovascular failure) or multiorgan failure. In the case of DIC, there is a massive activation of the coagulation system at the surface of damaged endothelial cells, the surfaces of foreign bodies or crosslinked extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

The binding molecules of the invention, preferably antibodies and antigen-binding fragments thereof, are also for use in the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

In addition, the binding molecules of the invention, preferably antibodies and antigen-binding fragments thereof, can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa.

The present invention further provides for the use of the binding molecules of the invention, preferably antibodies and antigen-binding fragments thereof, for the treatment and/or prophylaxis of disorders, especially the disorders mentioned above.

The present invention further provides for the use of the binding molecules of the invention, preferably antibodies and antigen-binding fragments thereof, for production of a medicament for the treatment and/or prophylaxis of disorders, especially the disorders mentioned above, preferably for producing a medicament for the treatment and/or prophylaxis of thrombotic or thromboembolic disorders.

The present invention further provides a method for the treatment and/or prophylaxis of disorders, especially the disorders mentioned above, using a therapeutically effective amount of a binding molecule of the invention, preferably an antibody and antigen-binding fragment thereof.

The present invention further provides the binding molecules of the invention, preferably antibodies and antigen-binding fragments thereof, for use in a method for the treatment and/or prophylaxis of disorders, especially the disorders mentioned above, using a therapeutically effective amount of a binding molecule of the invention, preferably antibody and antigen-binding fragment thereof.

The present invention further provides methods of treatment of thrombotic or thromboembolic disorders in man and/or animals by administration of a therapeutically effective amount of at least one binding molecule of the invention, preferably antibody and antigen-binding fragment thereof or a pharmaceutical composition of the invention. The present invention further provides a method of inhibiting blood coagulation, platelet aggregation and/or thrombosis in a subject by administration of a therapeutically effective amount of at least one binding molecule of the invention, preferably antibody and antigen-binding fragment thereof or a pharmaceutical composition of the invention.

Gene Therapy

Further provided herein is a transfer vector for use in mammalian gene therapy that comprises a polynucleotide as disclosed herein, and methods of treating or preventing disease comprising incorporating exogenous nucleic acid as described herein into the cell of a mammalian patient in need thereof, such that the exogenous nucleic acid is expressed and the disease is prevented or treated.

In one embodiment, nucleic acid molecules encoding both a heavy chain and a light chain are administered to a patient. In a preferred embodiment, the nucleic acid molecules are administered such that they are stably integrated into chromosomes of B cells because these cells are specialized for producing antibodies. In one embodiment, precursor B cells are transfected or infected ex vivo and re-transplanted into a patient in need thereof. In another embodiment, precursor B cells or other cells are infected in vivo using a recombinant virus known to infect the cell type of interest.

In a preferred embodiment, the gene therapy method comprises administering an isolated nucleic acid molecule encoding the heavy chain or an antigen-binding portion thereof of an anti-FXI antibody as disclosed herein and expressing the nucleic acid molecule. In another preferred embodiment, the gene therapy method comprises administering an isolated nucleic acid molecule encoding the light chain or an antigen-binding portion thereof of an anti-FXI antibody as disclosed herein and expressing the nucleic acid molecule. In another embodiment, the gene therapy method comprises administering an isolated nucleic acid molecule encoding the heavy chain or an antigen-binding portion thereof and an isolated nucleic acid molecule encoding the light chain or the antigen-binding portion thereof of an anti-FXI antibody as disclosed herein and expressing the nucleic acid molecule.

Specific conditions for the uptake of exogeneous nucleic acid are well known in the art. They include, but are not limited to, retroviral infection, adenoviral infection, transformation with plasmids, transformation with liposomes containing exogeneous nucleic acid, biolistic nucleic acid delivery (i.e. loading the nucleic acid onto gold or other metal particles and shooting or injecting into the cells), adeno-associated virus infection and Epstein-Barr virus infection. These may all be considered "expression vectors" for the purposes of the invention.

The expression vectors may be either extrachromosomal vectors or vectors which integrate into a host genome. Generally, these expression vectors include transcriptional and translational regulatory nucleic acid operably linked to the exogeneous nucleic acid. In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

In addition, the expression vector may comprise additional elements. For example, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

EXPERIMENTS

Figure 8:
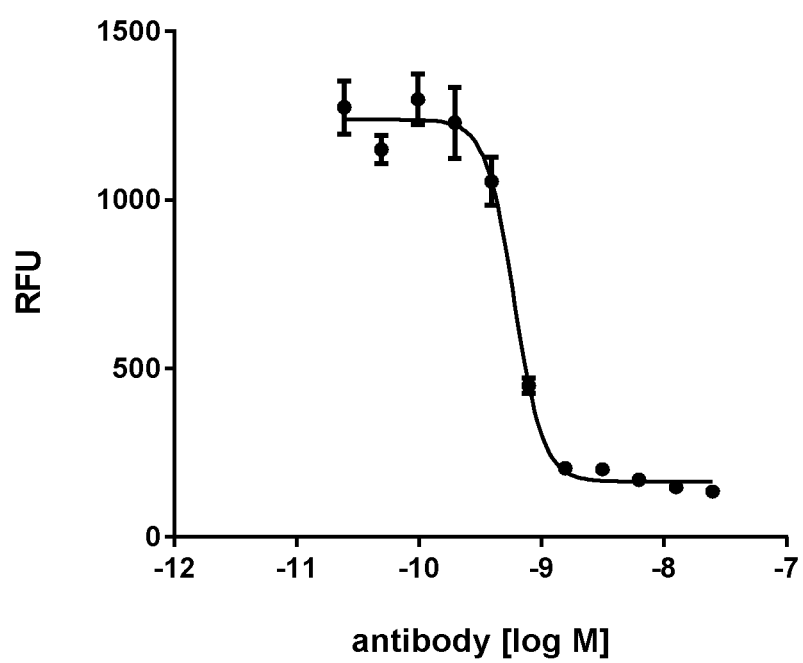
FIG. 8: Functional neutralization of the conversion of FXI into its active form, FXIa, by antibodies of this invention. Inhibition of the FXIIa induced conversion of FXI into its active form FXIa. Inhibitory activity (IC50 value) of the humanized and germlined anti-FXI antibody TPP-3583.

Starting from the murine 1A6 anti-FXI antibody, novel humanized antibodies (see Experiment 1) were generated. In order to further reduce the inherent immunogenicity potential, these antibodies were subjected to sequence optimization in the CDR regions as described below (experiment 2). Candidate antibodies were tested for their FXI binding activity determined by Enzyme-linked Immunosorbent Assays (ELISA) and by their ability to inhibit the conversion of FXI into its active form, FXIa (Experiments 4 and 5). For two exemplary antibodies, namely TPP-3290 and TPP-3238, EC50 values for ELISA and conversion assays are shown in FIG. 9. Obviously, the EC50 values are comparable to 1A6 thus those two antibodies seem to be valuable candidates for further exploration. Therefore, to confirm comparability to 1A6, antibodies TPP-3290 and TPP-3238 were tested in the in vivo baboon thrombosis model described in Experiment 10. Surprisingly, using reasonable pharmacological dosing regimens, these two antibodies did not show any antithrombotic activity. For both molecules, no reduction in the collagen-induced thrombus formation could be detected at all. In follow-up to this in vivo experiment, these antibodies were analyzed in the plasma based Activated Partial Thromboplastin Time (aPTT) test system. This type of analysis reconfirms the in vivo data in that way that for both antibodies only a very low or even no blocking effect was observed (Experiment 6 and FIG. 8). Thus, despite antibodies TPP-3290 and TPP-3238 having almost identical EC50 values in the ELISA and conversion assay compared to antibody 1A6 (see FIG. 9) they do not display an antithrombotic effect in vivo. There is no explanation readily available why 1A6 comparable ELISA and conversion assay values do not translate into anti-thrombotic activity in vivo or aPTT prolongation.

Figure 3:
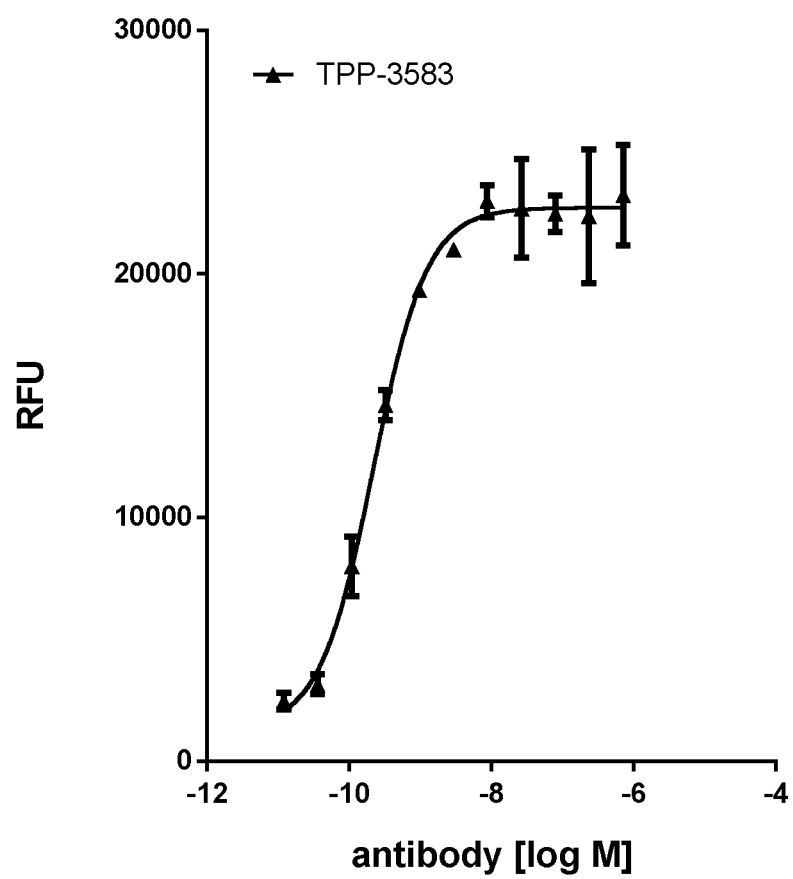
FIG. 3: Binding activities (EC50 value) of the humanized and germlined anti-FXI antibody TPP-3583 comprising SEQ ID NO: 17 for the amino acid sequence for the variable light chain domain and SEQ ID NO: 18 for the amino acid sequence for the variable heavy chain.
Figure 4:
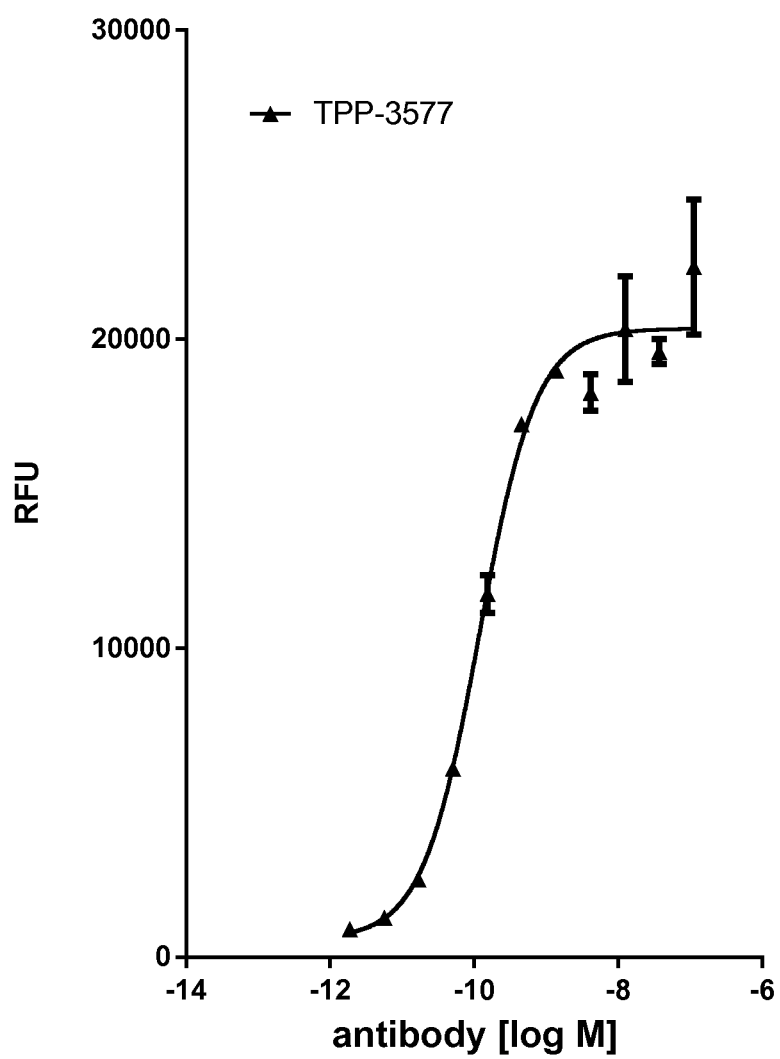
FIG. 4: Binding activities (EC50 value) of the humanized and germlined anti-FXI antibody TPP-3577 comprising SEQ ID NO: 19 for the amino acid sequence for the variable light chain domain and SEQ ID NO: 20 for the amino acid sequence for the variable heavy chain.
Figure 5:
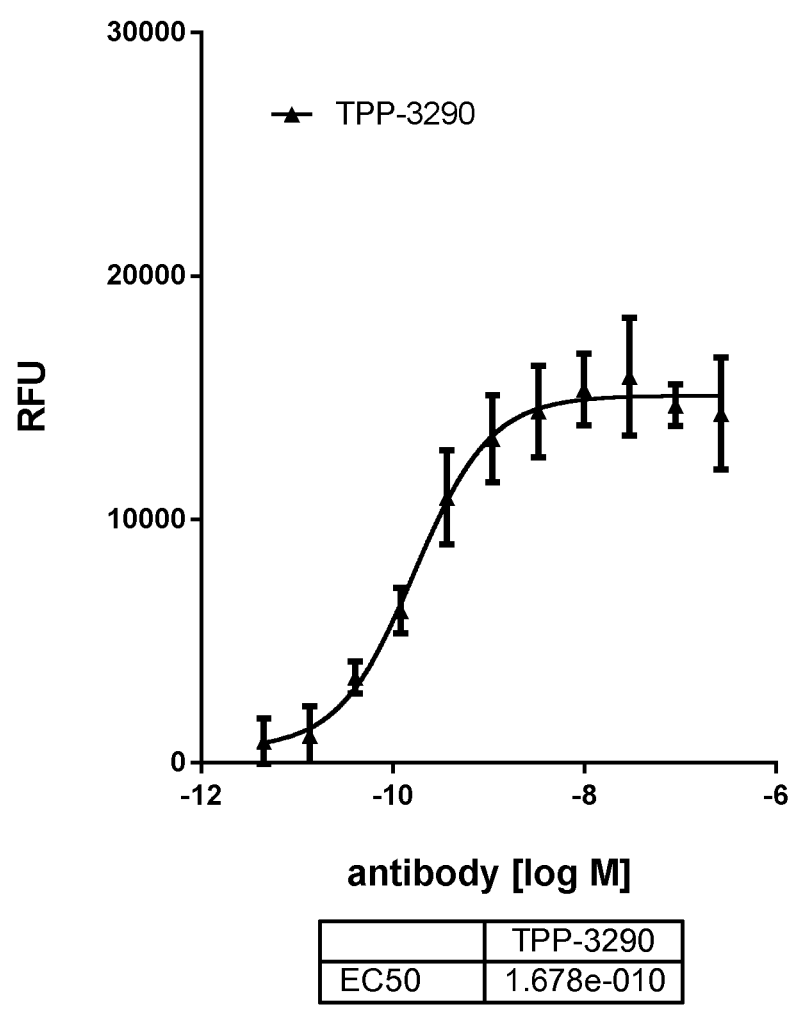
FIG. 5: Binding activities (EC50 value) of the humanized and germlined anti-FXI antibody TPP-3290 comprising SEQ ID NO: 21 for the amino acid sequence for the variable light chain domain and SEQ ID NO: 22 for the amino acid sequence for the variable heavy chain.
Figure 6:
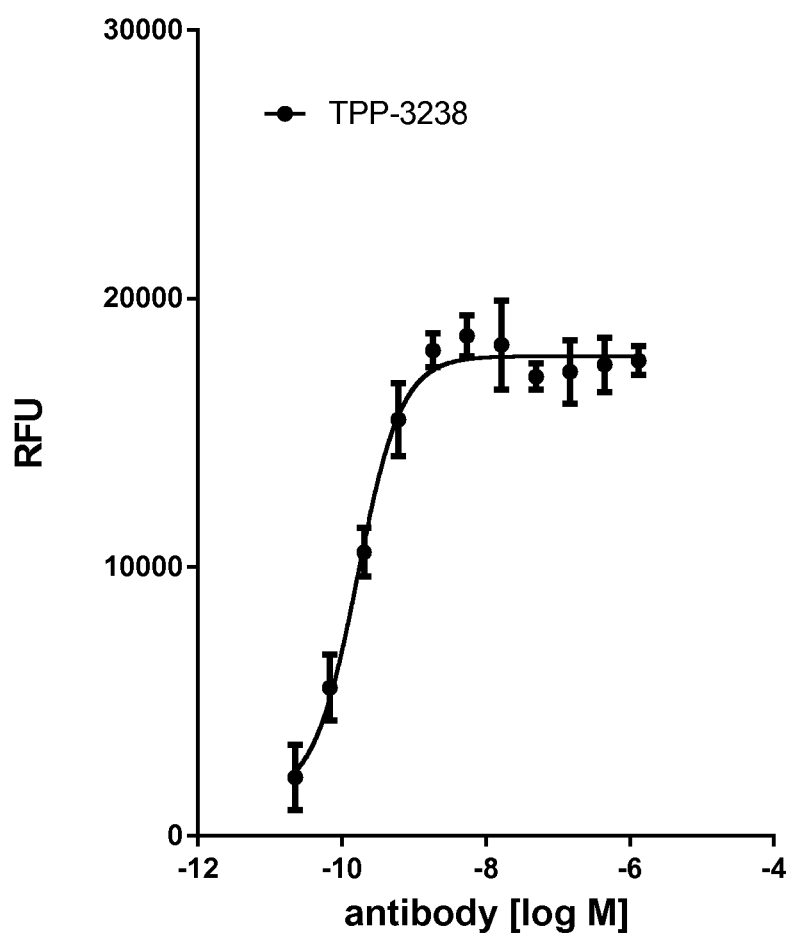
FIG. 6: Binding activities (EC50 value) of the humanized and germlined anti-FXI antibody TPP-3238 comprising SEQ ID NO: 23 for the amino acid sequence for the variable light chain domain and SEQ ID NO: 24 for the amino acid sequence for the variable heavy chain.

However, further sequence alterations lead to antibodies TTP-3583 and TTP-3577. These two antibodies exhibited excellent binding affinities to the target FXI (Experiment 3, FIGS. 3 and 4, FIG. 9). In addition antibodies TTP-3583 and TTP-3577 effectively block the conversion of FXI to its active form FXIa (Experiment 5 and FIGS. 7 and 8).

Surprisingly, antibodies TTP-3583 and TTP-3577 prolong the Activated Partial Thromboplastin Time (aPTT) at concentrations comparable to 1A6 or, in case of TPP-3583, at even lower concentrations (Experiment 6 and FIG. 9). Thus, two antibodies have been generated that in the biochemical assays in regard to their binding activity are comparable to the murine starting variant 1A6. TPP-3583 exhibited even slightly higher activity in the plasma based aPTT assay.

This was also confirmed by antithrombotic activity of TPP-3583 in in vivo model (see Experiment 9). Thus, with the provision of antibodies TPP-3583 and TPP-3577 the invention provides humanized and germlined antibodies that are both effective and expected to be safe for treatment, both in terms of a reduced immunogenicity and a minimization of bleeding risk. The antibodies evaluated herein are therefore promising new agents for effective treatment and/or prophylaxis of thrombotic or thromboembolic disorders and/or thrombotic or thromboembolic complications.

Experiment 1: Humanization of Murine Antibodies

Humanization of the murine antibody 1A6 was performed by using standard techniques.

In detail, for the selection of germline acceptor family subsets, CDR residues of the murine antibody were determined and annotated following the Kabat numbering system (for details see http://www.bioinf.org.uklabs/#kabatnum). The canonical structures of the heavy and light chain CDRs were determined based on the following publications:

O'Brien and Jones, Humanising Antibodies by CDR Grafting, Chapter 40; Antibody Engineering, Part of the series Springer Lab Manuals pp 567-590; R. Kontermann et al. (eds.), Antibody Engineering; Springer-Verlag Berlin Heidelberg 2001.

Hwang, Almagro, Buss, Tan, and Foote (2005) Use of human germline genes in a CDR homology-based approach to antibody humanization. Methods, May; 36(1):35-42.

Based on these publications, human germline framework acceptors with the same canonical structures were selected.

In a next step, residues were identified supporting loop structures and VH as well as VL interfaces based on the Kabat numbering system (for details see http://www.bioinf.org.uklabs/#kabatnum). Whenever necessary, amino acids which are important for loop conformation and for the $V_H$ and $V_L$ interfaces were back-mutated.

The identities and similarities to each individual human germline framework sequences within the same canonical subsets were analyzed and the germline sequence with the best overall homology to the murine $V_H$ and $V_L$ sequences were identified by using the Align X program of Vector NTI suite. These sequences were selected as accepter human germline framework for grafting $V_H$ and $V_L$ CDRs, respectively.

The human heavy chain joining region ($J_H$ region) as well as the human $V_L$ region was selected based on best sequence homology.

In order to analyze these in silico designed humanized variants for FXI binding activity, the corresponding cDNAs were synthesized and used for the expression of the humanized antibodies. For this, HEK293 cells were transfected with the cDNAs, and following 5 days of cultivation, antibodies were purified from the supernatant of these cells. Each purified humanized antibody was characterized for binding activity by using a standard ELISA protocol and for physicochemical properties by analyzing the molecules by size exclusion chromatography.

Experiment 2: Germlining and Sequence Optimization of CDRs

For further reduction of the intrinsic immunogenicity risk, in a next step germlining and sequence optimization of the CDRs of the humanized antibody was performed.

Therefore, amino acids which differ from the nearest germline sequence were exchanged, the corresponding cDNAs were synthesized, HEK293 cells were transiently transfected, the expressed antibodies of this invention were quantified and tested for their ability to bind human FXI (Haematologic Technologies Inc.; human FXI; Cat. No. HCXI-0150).

Experiment 3: Expression and Quantification of Antibody Variants

The above mentioned IgGs were transiently expressed in mammalian cells as described in Tom et al., Chapter 12 in Methods Express: Expression Systems edited by Micheal R. Dyson and Yves Durocher, Scion Publishing Ltd, 2007. Briefly, a CMV-Promoter based expression plasmid was transfected into HEK293-6E cells and incubated in Fernbach-Flasks or Wave-Bags. Transfected cells were cultivated at 37° C. for 5 to 6 days in F17 Medium (Invitrogen). 1% Ultra-Low IgG FCS (Invitrogen) and 0.5 mM valproic acid (Sigma) was supplemented 24 h post transfection. The antibodies were purified by Protein A chromatography and further characterized by their binding affinity using an Enzyme-linked immunosorbent assay (ELISA). See tables 1 and 2 infra for the sequences of the antibodies of the invention. Table 3 infra lists the sequences of further antibodies.

Experiment 4: Enzyme-linked Immunosorbent Assay (ELISA)

ELISA

A standard ELISA format was used for analyzing the binding affinity of antibodies of this invention to FXI. Human FXI was obtained from Haematologic Technologies Inc. (human FXI; Cat. No. HCXI-0150), baboon FXI was generated as described below. These antigens were coated to black 384 well Maxisorp microtiter plates (Nunc; Cat. No: 460518), diluted to a concentration of 1 µg/ml in 1× Coating Buffer (Candor Bioscience; Cat. No. 121125). Plates were incubated overnight at 4° C. After overnight incubation, plates were washed 2× with 50 µl/well using Phosphate Buffered Saline (PBS, SigmaAldrich, Cat. No. D8662)+ 0.05% Tween 20 (SigmaAldrich, Cat. No. P9416). Following this, 50 µl/well of blocking buffer (Smart Block; Candor Bioscience; Cat. No. 113500) was added and the plates incubated for 1 hour at room temperature. Afterwards, plates were washed for 3× using 50 µl/well of a PBS+0.05% Tween 20 buffer. Antibodies of this invention were added at different concentrations in a final volume of 30 µl/well. Plates were incubated for 1 hour at room temperature. Following this incubation step, plates were washed for 3× using 50 µl/well of a PBS+0.05% Tween 20 buffer. For the detection of bound candidate antibodies, the anti-h-Fc-POD antibody (Sigma; Cat. No. A0170) was diluted by the factor of 1:10000 in 10% Blocking Buffer. 30 µl/well of this diluted detection antibody was added and plates were incubated for 1 hour at room temperature. Following this incubation step, plates were washed for 3× using 50 µl/well of a PBS+0.05% Tween 20 buffer. As substrate, a mixture of 30 µl/well of 1:1000 diluted Amplex red (Invitrogen; Cat. No. 12222; stock solution 10 mM in DMSO) and 1:10000 of Hydrogen peroxide (Merck; Cat. No. 107209; 30% stock solution) was added and the plates were incubated for 20 minutes in the dark.

For measurement, the Infinite f500 reader (Tecan) was used.

Measurement Mode:
Fluorescence
Top reading
Ex 535 nm
Em 590 nm

Data were analyzed using the GraphPadPrism software, binding activity of this invention were calculated as EC50 values. All experiments were performed in quadruplicate, data are given as mean±SEM. Data for human FXI ELISA for the antibodies 1A6, TPP-3583, TPP-3577, TPP-3290, and TPP-3238 are shown in FIGS. 2-6 and numerical data in FIG. 9. Shape of the curves as well as EC50 values are comparable to 1A6 and therefore classified for further analysis.

Binding Domain Analysis Via Competitive EUSA

Figure 7:
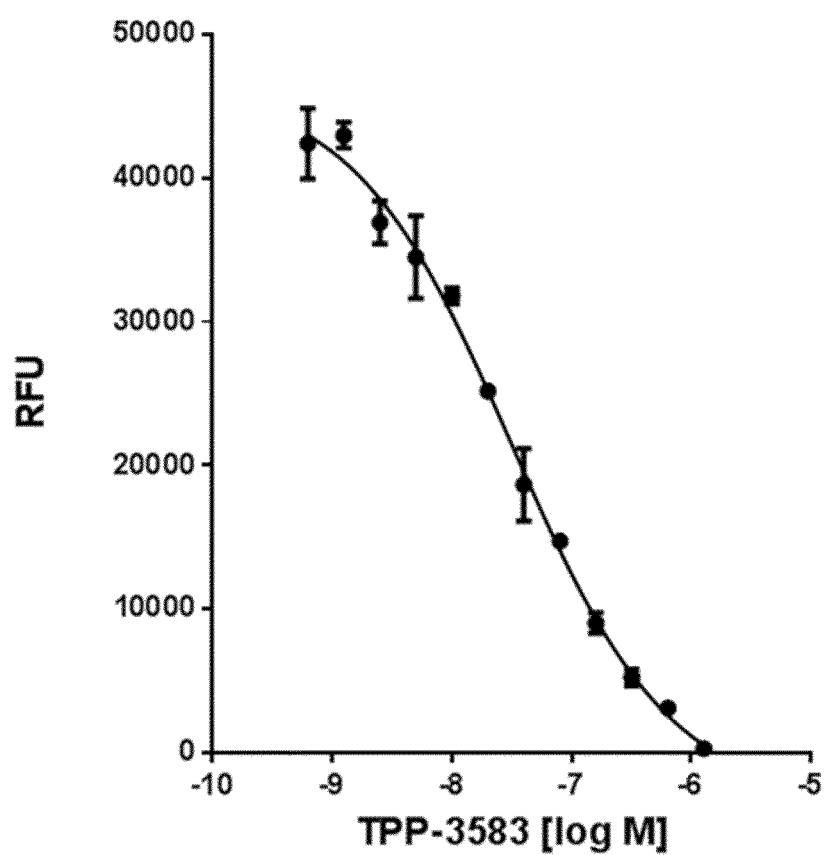
FIG. 7: Domain analysis via competitive ELISA assay for antibody TPP-3583.

In order to show, that humanized and optimized variants are still binding the same domain as the starting variant 1A6, competitive ELISA was used. For this, 1A6 was biotinylated by using the EZ-Link™ NHS-PEG4 Biotinylation Kit (ThermoFischer Scientific, Cat. No. 21455) according to the maufacture's instructions. As described above, FXI was coated and a fix concentration of biotiynlated 1A6 mixed with different concentrations of the antibodies of this invention were added. Binding of biotinylated 1A6 was detected by using HRP-Conjugated Streptavidin (SigmaAldrich, Cat. No. S5512). As substrate, a mixture of 30 µl/well of 1:1000 diluted Amplex red (Invitrogen; Cat. No. 12222; stock solution 10 mM in DMSO) and 1:10000 of Hydrogen peroxide (Merck; Cat. No. 107209; 30% stock solution) was added and the plates were incubated for 20 minutes in the dark. Binding of the antibodies of the invention to the same domain as 1A6 leads to displacement of the latter one by increasing concentrations of the humanized and optimized variants. This effect has been shown for all antibodies described in this invention. As example, the data of the competitive binding assay of TPP-3583 and 1A6 is shown in FIG. 7 indicating that these two antibodies bind to the same domain in the FXI molecule.

Generation of Baboon FXI cDNA for *Papio anubis* FXI (Uniprot Acc. No. A0A096NC95) was synthesized and cloned into mammalian expression vector pcDNA3.1(+) (ThermoFisher Scientific, Cat. No. V790-20). For expression and purification, HEK293 cells were transiently transfected by using the Lipofectamine LTX Reagent with PLUS Reagent (Invitrogen, CatNo. A12621) following the manufactures' instructions. Recombinant expression of baboon FXI was analyzed by SDS-PAGE. Binding activities of antibodies described in this invention to baboon FXI binding are shown in FIG. 9.

Experiment 5: Functional Neutralization of the Conversion of FXI into its Active Form, FXIa, by Antibodies of this Invention For testing the inhibition of the conversion of FXI (Haematologic Technologies, Inc., catalogue number HCXIA-0150) into its active form FXIa by FXIIa, 10 nM of human FXI was incubated in 50 mM Tris/HCl, 100 mM NaCl, 5 mM CaCl2 und 0.1% BSA with different concentrations of the antibodies for 1 hour at 37° C. In a next step, human FXIIa (Enzyme Research, catalogue number HFXIIa 1212a) at a final concentration of 1 unit/mg was added and incubated for 24 hours at 37° C. Next, Corn Trypsin Inhibitor (Enzyme Research, CTI) at a final concentration of 200 nM and the fluorogenically-labeled substrate (1-1575, Bachem, final concentration 25 µM) were added. The fluorescence was monitored continuously at 360/465 nm using a SpectraFluorplus Reader (Tecan). Data were analyzed using the GraphPadPrism software. Data are given as mean±SEM, n=4 (see graph for TPP-3583 in FIG. 8, numerical values for other antibodies are listed in FIG. 9).

Experiment 6: Activated Partial Thromboplastin Time (aPTT)

Aliquots of human plasma were incubated with increasing concentrations of the antibodies of this invention for 3 min at 37° C. To initiate the intrinsic coagulation pathway, 0.05 ml of plasma was incubated with 0.05 ml of aPTT reagent (Diagnostica Stago, K.C Prest 5) for exactly 3 min. Coagulation was started by recalcifying the samples with 0.05 ml of 0.025 M prewarmed calcium chloride solution. An automated coagulometer (AMAX 200, Trinity Biotech, Lemgo, Germany) mixed the plasma at 37° C. and mechanically recorded the time to clotting. The test drug concentration prolonging aPTT by a factor of 1.5 was calculated and reported. (FIG. 9).

Experiment 9: In Vivo Baboon Thrombosis Model

Figure 10:
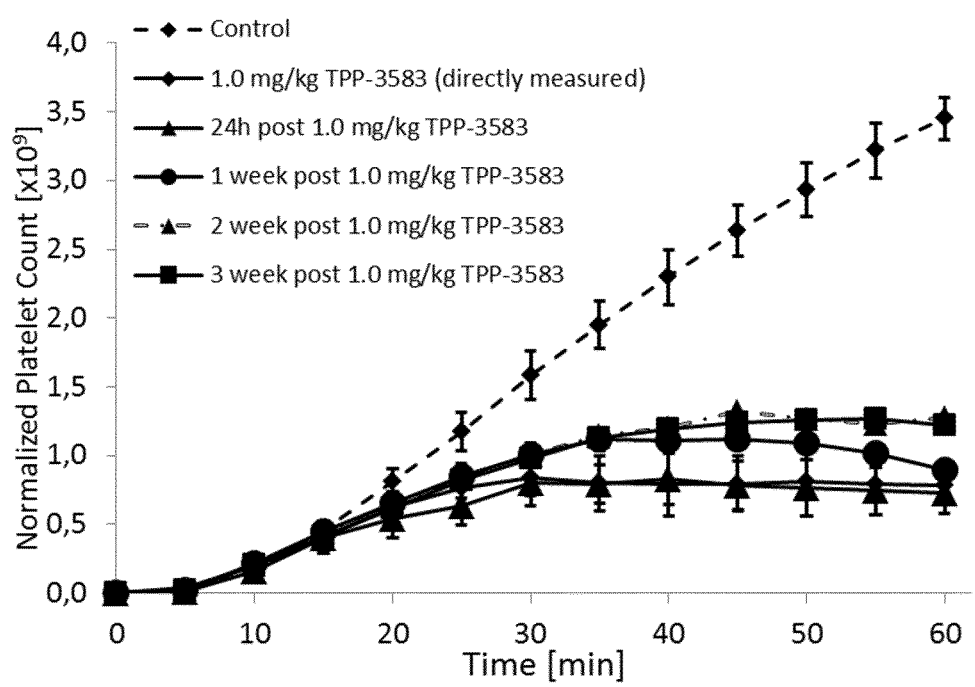
FIG. 10: in vivo measurement of platelet deposition on collagen-coated vascular grafts following TPP3583 i.v. application.

In a baboon AV-shunt model, thrombus formation was initiated by temporal deployment of a thrombogenic device into the hypothrombogenic chronic AV shunt. The thrombogenic device that was used to evaluate the effect of antibodies on thrombus initiation and propagation consisted of a 4 mm internal diameter (i.d.), 20 mm long collagen-coated ePTFE graft that was followed by a 9 mm i.d., 20 mm long silicone rubber expansion chamber. The shear rate in the graft was meant to mimic arterial-type blood coagulation and the shear rate in the expansion chamber was meant to mimic venous-type blood coagulation. Thrombus formation was assessed in real time during the experiments by quantitative gamma camera imaging of radiolabeled platelet accumulation within the graft segment, and by end-point determinations of radiolabeled fibrinogen/fibrin deposition (for further details see Tucker et al. Blood. 2009 Jan. 22; 113(4):936-944, page 937, left column, chapter headed by "Thrombosis model"). As shown in FIG. 10, the intravenous application of 1 mg/kg in phosphate buffered saline (PBS) of TPP-3583 led to a reduction of platelet deposition by approximately 80%. These data are comparable to the anti-thrombotic activity of the murine 1A6 antibody as published by Tucker et al. (Blood. 2009 Jan. 22; 113(4):936-944).

Figure 11:
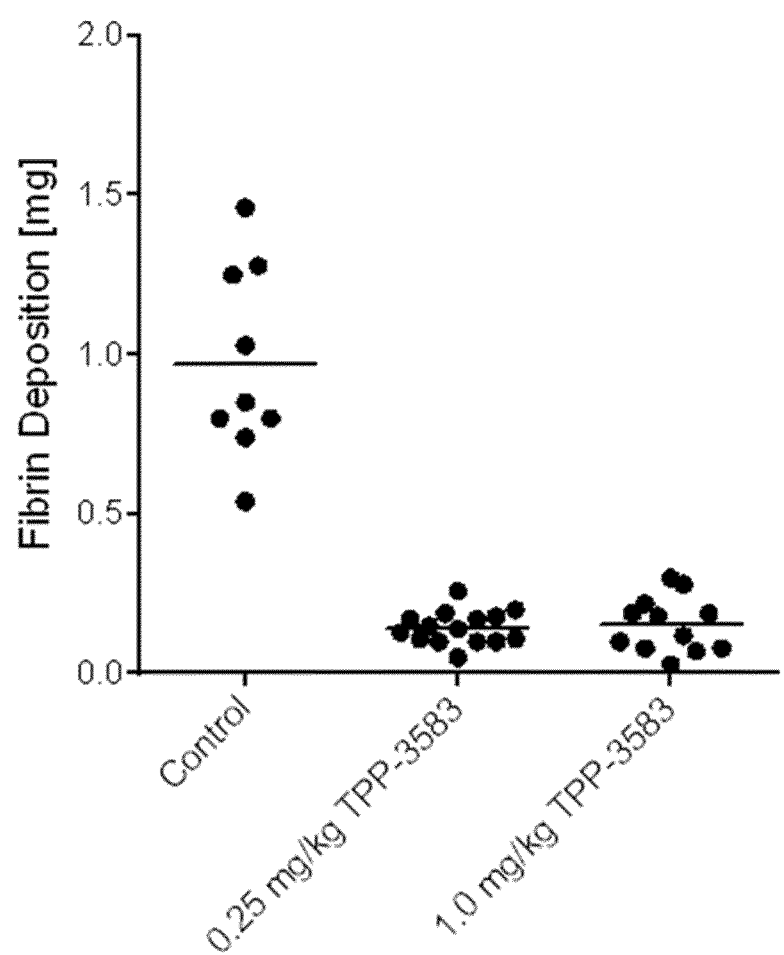
FIG. 11: in vivo measurement of fibrin deposition on collagen-coated vascular grafts following TPP3583 i.v. application.

Beneath the inhibition of platelet deposition, administration of TPP-3583 also led to a significant reduction of fibrin accumulation in the collagen coated graft by approximately 80% (FIG. 11).

Further preferred embodiments are

1. A Binding Molecule Comprising (a) a CDR1 of the light chain comprising the sequence
(SEQ ID NO: 8)
KASQSVLYSGDNYLN;

(b) a CDR2 of the light chain comprising the sequence
(SEQ ID NO: 9)
AASTLES;

(c) a CDR3 of the light chain comprising the sequence
(SEQ ID NO: 10)
QQYNGDPWT;

(d) a CDR1 of the heavy chain comprising the sequence
(SEQ ID NO: 11)
TSGMGVG;

(e) a CDR2 of the heavy chain comprising the sequence
(SEQ ID NO: 12)
HIDWDDDKYYSPSLKS;
and

TABLE 1 polypeptide sequences of antibodies TPP-3583 and TPP-3577

| antibody | SEQ ID NO: | | | | | | | | | |
|---|---|---|---|---|---|---|---|---|---|---|
| | CDRL1 | CDRL2 | CDRL3 | CDRH1 | CDRH2 | CDRH3 | VL | VH | Light Chain | Heavy Chain |
| TPP-3583 | 8 | 9 | 10 | 11 | 12 | 13 | 17 | 18 | 27 | 28 |
| TPP-3577 | 14 | 9 | 10 | 11 | 15 | 16 | 19 | 20 | 29 | 30 |

TABLE 2 polynucleotide sequences of antibodies TPP-3583 and TPP-3577

| antibody | SEQ ID NO: | | | | | | | | | |
|---|---|---|---|---|---|---|---|---|---|---|
| | CDRL1 | CDRL2 | CDRL3 | CDRH1 | CDRH2 | CDRH3 | VL | VH | Light Chain | Heavy Chain |
| TPP-3583 | — | — | — | — | — | — | 31 | 32 | — | — |
| TPP-3577 | — | — | — | — | — | — | 33 | 34 | — | — |

TABLE 3 polypeptide sequences of further antibodies

| antibody | SEQ ID NO: | | | | | | | | | |
|---|---|---|---|---|---|---|---|---|---|---|
| | CDRL1 | CDRL2 | CDRL3 | CDRH1 | CDRH2 | CDRH3 | VL | VH | Light Chain | Heavy Chain |
| 1A6 | 1 | 2 | 3 | 4 | 5 | 6 | 25 | 26 | — | — |
| TPP-3290 | — | — | — | — | — | — | 21 | 22 | 35 | 36 |
| TPP-3238 | — | — | — | — | — | — | 23 | 24 | 37 | 38 |

(f) a CDR3 of the heavy chain comprising the
sequence
IRSSVYAHYYGMDY (SEQ ID NO: 13)

Preferably, the binding molecule is a monoclonal antibody or antigen binding fragment thereof comprising an antigen-binding site of the light chain that comprises
(a) a CDR1 of the light chain comprising the sequence as depicted in SEQ ID NO: 8;
(b) a CDR2 of the light chain comprising the sequence as depicted in SEQ ID NO: 9; and
(c) a CDR3 of the light chain comprising the sequence as depicted in SEQ ID NO: 10;
and an antigen-binding site of the heavy chain that comprises
(a) a CDR1 of the heavy chain comprising the sequence as depicted in SEQ ID NO: 11;
(b) a CDR2 of the heavy chain comprising the sequence as depicted in SEQ ID NO: 12; and
(c) a CDR3 of the heavy chain comprising the sequence as depicted in SEQ ID NO: 13.

2. The binding molecule according to embodiment 1, which is capable of binding to Factor XI and/or Factor XIa. Preferably, the binding molecule according to embodiment 1 binds specifically to Factor XI and/or Factor XIa.

3. The binding molecule according to embodiment 1 or 2, wherein said Factor XI or Factor XIa is a primate Factor XI or primate Factor XIa.

4. The binding molecule according to embodiment 3, wherein said primate is a human or a non-human primate.

5. The binding molecule according to embodiment 4, wherein said non-human primate is a baboon, chimpanzee, gorilla, orangutan, cynomolgus macaque or rhesus macaque.

6. The binding molecule of any one of the preceding embodiments, wherein said binding molecule binds within an amino acid sequence corresponding to the A3 domain of Factor XI comprising amino acids 200 to 283 of SEQ ID NO: 7

7. The binding molecule according to any one of the preceding claims, wherein said binding molecule binds to an epitope within an amino acid sequence corresponding to a) amino acids 201 to 215 of SEQ ID NO:7; b) amino acids 221 to 222 of SEQ ID NO:7; c) amino acids 252 to 254 of SEQ ID NO:7; d) amino acids 259 to 261 of SEQ ID NO:7; e) amino acids 270 to 272 of SEQ ID NO:7; and/or f) amino acids 276 to 278 of SEQ ID NO:7.

8. The binding molecule according to any one of the preceding embodiments comprising a $V_L$ region as depicted in SEQ ID NO: 17.

9. The binding molecule according to any one of the preceding embodiments, wherein the binding molecule comprises a $V_H$ region as depicted in SEQ ID NO: 18.

10. The binding molecule according to any one of the preceding embodiments comprising a $V_L$ region as depicted in SEQ ID NO: 17 and a $V_H$ region as depicted in SEQ ID NO: 18.

11. The binding molecule according to any one of the preceding embodiments, wherein the binding molecule comprises a light chain as depicted in SEQ ID NO: 27.

12. The binding molecule according to any one of the preceding embodiments, wherein said binding molecule comprises a heavy chain as depicted in SEQ ID NO: 28.

13. The binding molecule according to any one of the preceding embodiments, wherein the binding molecule comprises a light chain as depicted in SEQ ID NO: 27 and a heavy chain as depicted in SEQ ID NO:28.

14. The binding molecule according to any one of the preceding embodiments, wherein said binding molecule is an antibody.

15. The binding molecule according to any one of the preceding embodiments, wherein said antibody is a monoclonal antibody or antigen-binding fragment thereof.

16. The binding molecule according to embodiment 15, wherein said monoclonal antibody is a humanized monoclonal antibody or a chimeric monoclonal antibody.

Preferably, the humanized monoclonal antibody is an antibody with all variable domain and all constant domain framework regions of human origin.

17. The binding molecule according to any one of embodiments 14 to 16, wherein said antibody is an IgG, preferably an IgG1 or IgG4.

18. A polynucleotide encoding a binding molecule as defined in any of embodiments 1 to 17.

19. A vector, which comprises a polynucleotide as defined in embodiment 18.

20. The vector according to embodiment 19, wherein said vector further comprises at least one regulatory sequence which is operably linked to said polynucleotide defined in embodiment 18.

21. The vector according to embodiment 19 or 20, wherein said vector is an expression vector.

22. A host cell comprising a vector according to any one of embodiments 19 to 21 and/or a nucleic acid according to embodiment 18.

23. A process for the production of a binding molecule according to any of embodiments 1 to 17, said process comprising culturing a host cell defined in embodiment 22 under conditions allowing the expression of the binding molecule as defined in any of embodiments 1 to 17 and optionally recovering the produced binding molecule from the culture.

24. A pharmaceutical composition comprising a binding molecule according to any one of embodiments 1 to 17 or produced according to the process of embodiment 23, the polynucleotide of claim 18, the vector of embodiment 19 to 21, and/or the host cell of embodiment 22, and optionally a pharmaceutically acceptable excipient.

25. The pharmaceutical composition according to embodiment 24, further comprising one or more additional active agent.

26. The pharmaceutical composition according to embodiment 25, wherein the further additional active agent is selected from plasminogen activators (thrombolytics/fibrinolytics); inhibitors of plasminogen activators; inhibitors of thrombin-activated fibrinolysis inhibitors (TAFI) including tissue plasminogen activator (t-PA), streptokinase, reteplase, and urokinase; non-fractionated heparins; low molecular weight Heparins; Heparinoid; Hirudin; Bivalirudin and/or Argatroban.

27. The binding molecule according to any one of embodiments 1 to 17 or produced according to the process of embodiment 23, the polynucleotide according to embodiment 18, the vector according to any one of embodiments 19 to 21, the host cell according to embodiment 22 or the pharmaceutical composition according to any one of embodiments 24 to 26 for use as a medicament.

28. The binding molecule according to any one of embodiments 1 to 17 or produced according to the process of embodiment 23, the polynucleotide according to embodiment 18, the vector according to any one of embodiments 19 to 21, the host cell according to embodiment 22 or the pharmaceutical composition according to any one of embodiments 24 to 26 for use in the treatment and/or prophylaxis of thrombotic or thromboembolic disorders and/or thrombotic or thromboembolic complications.

29. The binding molecule according to any one of embodiments 1 to 17 or produced according to the process of embodiment 23, the polynucleotide according to embodiment 18, the vector according to any one of embodiments 19 to 21, the host cell according to embodiment 22 or the pharmaceutical composition to any one of embodiments 24 to 26 for use in a method of inhibiting blood coagulation, platelet aggregation and/or thrombosis in a subject.

30. Use of the binding molecule according to any one of embodiments 1 to 17 or produced according to embodiment 23 as an anticoagulant in blood samples, blood preservations, plasma products, biological samples, or medicinal additives or devices.

31. A kit comprising a binding molecule according to any one of embodiments 1 to 17, or produced according to the process of embodiment 23, a polynucleotide according to embodiment 18, a vector according to any one of embodiments 19 to 21, a host cell according to embodiment 22 or the pharmaceutical composition according to anyone of embodiments 24 to 26.

The invention claimed is:

1. A monoclonal antibody or an antigen-binding fragment thereof, which specifically binds human Factor XI and/or human Factor XIa comprising

```
(a) a CDR1 of the light chain comprising the
sequence
                                    (SEQ ID NO: 8)
KASQSVLYSGDNYLN;

(b) a CDR2 of the light chain comprising the
sequence
                                    (SEQ ID NO: 9)
AASTLES;
and (c) a CDR3 of the light chain comprising the
sequence
                                    (SEQ ID NO: 10)
QQYNGDPWT;

(d) a CDR1 of the heavy chain comprising the
sequence
                                    (SEQ ID NO: 11)
TSGMGVG;

(e) a CDR2 of the heavy chain comprising the
sequence
                                    (SEQ ID NO: 12)
HIDWDDDKYYSPSLKS;
and (f) a CDR3 of the heavy chain comprising the
sequence
                                    (SEQ ID NO: 13)
IRSSVYAHYYGMDY.
```

2. The monoclonal antibody or an antigen-binding fragment thereof according to claim 1 comprising a $V_L$ region as depicted in SEQ ID NO: 17.

3. The monoclonal antibody or an antigen-binding fragment thereof according to claim 1, wherein the monoclonal antibody comprises a $V_H$ region as depicted in SEQ ID NO: 18.

4. The monoclonal antibody or an antigen-binding fragment thereof according to claim 1, wherein the monoclonal antibody comprises a $V_L$ region as depicted in SEQ ID NO: 17 and a $V_H$ region as depicted in SEQ ID NO: 18.

5. The monoclonal antibody or an antigen-binding fragment thereof according to claim 1, wherein the monoclonal antibody comprises a light chain as depicted in SEQ ID NO: 27.

6. The monoclonal antibody or an antigen-binding fragment thereof according to claim 1, wherein the monoclonal antibody comprises a heavy chain as depicted in SEQ ID NO: 28.

7. The monoclonal antibody or an antigen-binding fragment thereof according to claim 1, wherein the monoclonal antibody comprises a light chain as depicted in SEQ ID NO: 27 and a heavy chain as depicted in SEQ ID NO: 28.

8. The monoclonal antibody or an antigen-binding fragment thereof according to claim 1, wherein the monoclonal antibody is a humanized monoclonal antibody or a chimeric monoclonal antibody.

9. The monoclonal antibody or antigen-binding fragment thereof according to claim 1, wherein the monoclonal antibody is an IgG, preferably an IgG1 or IgG4.

10. A polynucleotide encoding the monoclonal antibody or antigen-binding fragment thereof of claim 1.

11. A vector, which comprises the polynucleotide of claim 10.

12. A culture comprising a host cell that comprises the nucleic acid according to claim 10.

13. A process for the production of a monoclonal antibody or antigen-binding fragment, said process comprising culturing the culture comprising the host cell of claim 12 under conditions allowing the expression of the monoclonal antibody or antigen-binding fragment thereof.

14. A pharmaceutical composition comprising the monoclonal antibody or antigen-binding fragment produced according to the process of claim 13 and a pharmaceutically acceptable excipient.

15. A pharmaceutical composition comprising the monoclonal antibody or antigen-binding fragment thereof according to claim 1 and a pharmaceutically acceptable excipient.

16. The pharmaceutical composition according to claim 14, further comprising one or more additional active agent.

17. A method of using the monoclonal antibody or antigen-binding fragment thereof according to claim 1 as a medicament comprising administering the monoclonal antibody or antigen-binding fragment thereof to a subject in need of the medicament.

18. The method of claim 17, wherein the subject needs treatment of thrombotic or thromboembolic disorders and/or thrombotic or thromboembolic complications.

19. A kit comprising the monoclonal antibody or antigen-binding fragment thereof according to claim 1 in lyophilized form and a pharmaceutically acceptable carrier for resuspension of the monoclonal antibody or antigen-binding fragment thereof.

20. The process of claim 13 further comprising recovering the produced antibody or antigen-binding fragment thereof from the culture.

* * * * *

```
                        SEQUENCE LISTING

<160> NUMBER OF SEQ ID NOS: 38

<210> SEQ ID NO 1
<211> LENGTH: 15
<212> TYPE: PRT
<213> ORGANISM: Mus musculus

<400> SEQUENCE: 1

Lys Ala Ser Gln Ser Val Asp Tyr Asp Gly Asp Ser Tyr Leu Asn
1               5                   10                  15

<210> SEQ ID NO 2
<211> LENGTH: 7
<212> TYPE: PRT
<213> ORGANISM: Mus musculus

<400> SEQUENCE: 2

Ala Ala Ser Asn Leu Glu Ser
1               5

<210> SEQ ID NO 3
<211> LENGTH: 7
<212> TYPE: PRT
<213> ORGANISM: Mus musculus

<400> SEQUENCE: 3

Gln Gln Ser Asn Gly Asp Pro
1               5

<210> SEQ ID NO 4
<211> LENGTH: 12
<212> TYPE: PRT
<213> ORGANISM: Mus musculus

<400> SEQUENCE: 4

Gly Phe Ser Leu Ser Thr Ser Gly Met Gly Val Gly
1               5                   10

<210> SEQ ID NO 5
<211> LENGTH: 12
<212> TYPE: PRT
<213> ORGANISM: Mus musculus

<400> SEQUENCE: 5

His Ile Trp Trp Asp Asp Asp Lys Tyr Tyr Asn Pro
1               5                   10

<210> SEQ ID NO 6
<211> LENGTH: 13
<212> TYPE: PRT
<213> ORGANISM: Mus musculus
```

-continued

<400> SEQUENCE: 6

Lys Arg Ser Ser Val Val Ala His Tyr Tyr Ala Met Asp
1               5                   10

<210> SEQ ID NO 7
<211> LENGTH: 625
<212> TYPE: PRT
<213> ORGANISM: Homo sapiens

<400> SEQUENCE: 7

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
                20                  25                  30

Gly Asp Ile Thr Thr Val Phe Thr Pro Ser Ala Lys Tyr Cys Gln Val
            35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Cys Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

```
Asn Gly Ser Pro Thr Lys Ile Leu His Gly Arg Gly Ile Ser Gly
        355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
            435                 440                 445

Leu Asn Gln Ser Glu Ile Lys Glu Asp Thr Ser Phe Phe Gly Val Gln
        450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
        515                 520                 525

Gln Asn Thr Leu Gln Lys Ala Lys Ile Pro Leu Val Thr Asn Glu Glu
    530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
    610                 615                 620

Val
625

<210> SEQ ID NO 8
<211> LENGTH: 15
<212> TYPE: PRT
<213> ORGANISM: Artificial Sequence
<220> FEATURE:
<223> OTHER INFORMATION: Humanized

<400> SEQUENCE: 8

Lys Ala Ser Gln Ser Val Leu Tyr Ser Gly Asp Asn Tyr Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Humanized

<400> SEQUENCE: 9

Ala Ala Ser Thr Leu Glu Ser
```

```
1               5

<210> SEQ ID NO 10
<211> LENGTH: 9
<212> TYPE: PRT
<213> ORGANISM: Artificial Sequence
<220> FEATURE:
<223> OTHER INFORMATION: Humanized

<400> SEQUENCE: 10

Gln Gln Tyr Asn Gly Asp Pro Trp Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Humanized

<400> SEQUENCE: 11

Thr Ser Gly Met Gly Val Gly
1               5

<210> SEQ ID NO 12
<211> LENGTH: 16
<212> TYPE: PRT
<213> ORGANISM: Artificial Sequence
<220> FEATURE:
<223> OTHER INFORMATION: Humanized

<400> SEQUENCE: 12

His Ile Asp Trp Asp Asp Asp Lys Tyr Tyr Ser Pro Ser Leu Lys Ser
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Humanized

<400> SEQUENCE: 13

Ile Arg Ser Ser Val Tyr Ala His Tyr Tyr Gly Met Asp Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Humanized

<400> SEQUENCE: 14

Lys Ser Ser Gln Ser Val Leu Tyr Ser Gly Asp Asn Tyr Leu Asn
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Humanized

<400> SEQUENCE: 15

His Ile Asp Trp Asp Asp Asp Lys Tyr Tyr Ser Thr
1               5                   10
```

```
<210> SEQ ID NO 16
<211> LENGTH: 14
<212> TYPE: PRT
<213> ORGANISM: Artificial Sequence
<220> FEATURE:
<223> OTHER INFORMATION: Humanized

<400> SEQUENCE: 16

Ile Arg Ser Ser Val Tyr Ala His Tyr Tyr Gly Met Asp Val
 1               5                  10

<210> SEQ ID NO 17
<211> LENGTH: 111
<212> TYPE: PRT
<213> ORGANISM: Artificial Sequence
<220> FEATURE:
<223> OTHER INFORMATION: Humanized

<400> SEQUENCE: 17

Asp Ile Val Met Thr Gln Ser Pro Asp Ser Leu Ala Val Ser Leu Gly
 1               5                  10                  15

Glu Arg Ala Thr Ile Ser Cys Lys Ala Ser Gln Ser Val Leu Tyr Ser
             20                  25                  30

Gly Asp Asn Tyr Leu Asn Trp Tyr Gln Gln Lys Pro Gly Gln Pro Pro
         35                  40                  45

Lys Leu Leu Ile Tyr Ala Ala Ser Thr Leu Glu Ser Gly Ile Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Tyr Asn
                 85                  90                  95

Gly Asp Pro Trp Thr Phe Gly Gly Gly Thr Lys Val Glu Ile Lys
            100                 105                 110

<210> SEQ ID NO 18
<211> LENGTH: 124
<212> TYPE: PRT
<213> ORGANISM: Artificial Sequence
<220> FEATURE:
<223> OTHER INFORMATION: Humanized

<400> SEQUENCE: 18

Glu Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Gly Trp Ile Arg Gln Pro Pro Gly Lys Ala Leu Glu
         35                  40                  45

Trp Leu Ala His Ile Asp Trp Asp Asp Lys Tyr Tyr Ser Pro Ser
     50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Arg Ser Ser Val Tyr Ala His Tyr Tyr Gly Met Asp
            100                 105                 110

Tyr Trp Gly Gln Gly Thr Thr Val Thr Val Ser Ser
        115                 120
```

```
<210> SEQ ID NO 19
<211> LENGTH: 111
<212> TYPE: PRT
<213> ORGANISM: Artificial Sequence
<220> FEATURE:
<223> OTHER INFORMATION: Humanized

<400> SEQUENCE: 19

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Val Leu Tyr Ser
            20                  25                  30

Gly Asp Asn Tyr Leu Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Asn
                85                  90                  95

Gly Asp Pro Trp Thr Phe Gly Gly Gly Thr Lys Val Glu Ile Lys
            100                 105                 110

<210> SEQ ID NO 20
<211> LENGTH: 124
<212> TYPE: PRT
<213> ORGANISM: Artificial Sequence
<220> FEATURE:
<223> OTHER INFORMATION: Humanized

<400> SEQUENCE: 20

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Gly Trp Ile Arg Gln Pro Pro Gly Lys Ala Leu Glu
        35                  40                  45

Trp Leu Ala His Ile Asp Trp Asp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ser Ser Val Tyr Ala His Tyr Tyr Gly Met Asp
            100                 105                 110

Val Trp Gly Gln Gly Thr Thr Val Thr Val Ser Ser
        115                 120

<210> SEQ ID NO 21
<211> LENGTH: 111
<212> TYPE: PRT
<213> ORGANISM: Artificial Sequence
<220> FEATURE:
<223> OTHER INFORMATION: Humanized

<400> SEQUENCE: 21

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Leu Tyr Ser
            20                  25                  30
```

```
                    20                  25                  30

Gly Asp Asn Tyr Leu Asn Trp Tyr Gln Gln Lys Pro Gly Gln Pro Pro
                35                  40                  45

Lys Leu Leu Ile Tyr Ala Ala Ser Thr Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Asn
                85                  90                  95

Gly Thr Pro Trp Thr Phe Gly Gly Gly Thr Lys Val Glu Ile Lys
            100                 105                 110

<210> SEQ ID NO 22
<211> LENGTH: 124
<212> TYPE: PRT
<213> ORGANISM: Artificial Sequence
<220> FEATURE:
<223> OTHER INFORMATION: Humanized

<400> SEQUENCE: 22

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45

Trp Leu Ala His Ile Asp Trp Asp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ser Ser Val Tyr Ala His Tyr Tyr Gly Met Asp
            100                 105                 110

Tyr Trp Gly Gln Gly Thr Thr Val Thr Val Ser Ser
        115                 120

<210> SEQ ID NO 23
<211> LENGTH: 111
<212> TYPE: PRT
<213> ORGANISM: Artificial Sequence
<220> FEATURE:
<223> OTHER INFORMATION: Humanized

<400> SEQUENCE: 23

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Val Leu Tyr Ser
                20                  25                  30

Ser Asn Asn Tyr Leu Asn Trp Tyr Gln Gln Lys Pro Gly Gln Pro Pro
            35                  40                  45

Lys Leu Leu Ile Tyr Ala Ala Ser Thr Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95
```

```
Ser Thr Pro Trp Thr Phe Gly Gly Gly Thr Lys Val Glu Ile Lys
            100                 105                 110

<210> SEQ ID NO 24
<211> LENGTH: 124
<212> TYPE: PRT
<213> ORGANISM: Artificial Sequence
<220> FEATURE:
<223> OTHER INFORMATION: Humanized

<400> SEQUENCE: 24

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Asp Trp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ser Ser Val Tyr Tyr Tyr Tyr Gly Met Asp
            100                 105                 110

Val Trp Gly Gln Gly Thr Thr Val Thr Val Ser Ser
        115                 120

<210> SEQ ID NO 25
<211> LENGTH: 111
<212> TYPE: PRT
<213> ORGANISM: Mus musculus

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Gly Asp Pro Trp Thr Phe Gly Gly Gly Thr Lys Leu Glu Ile Lys
            100                 105                 110

<210> SEQ ID NO 26
<211> LENGTH: 124
<212> TYPE: PRT
<213> ORGANISM: Mus musculus

<400> SEQUENCE: 26

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30
```

Gly Met Gly Val Gly Trp Ile Arg Gln Pro Ser Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Ala Ala Asp Thr Ala Thr Tyr Tyr
                85                  90                  95

Cys Ala Arg Lys Arg Ser Ser Val Val Ala His Tyr Tyr Ala Met Asp
            100                 105                 110

Tyr Trp Gly Gln Gly Thr Ser Val Thr Val Ser Ser
            115                 120

<210> SEQ ID NO 27
<211> LENGTH: 218
<212> TYPE: PRT
<213> ORGANISM: Artificial Sequence
<220> FEATURE:
<223> OTHER INFORMATION: Humanized

<400> SEQUENCE: 27

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Leu Tyr Ser
            20                  25                  30

Gly Asp Asn Tyr Leu Asn Trp Tyr Gln Gln Lys Pro Gly Gln Pro Pro
            35                  40                  45

Lys Leu Leu Ile Tyr Ala Ala Ser Thr Leu Glu Ser Gly Ile Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Asn
                85                  90                  95

Gly Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 28
<211> LENGTH: 453
<212> TYPE: PRT
<213> ORGANISM: Artificial Sequence
<220> FEATURE:
<223> OTHER INFORMATION: Humanized

<400> SEQUENCE: 28

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Asp Trp Asp Asp Lys Tyr Tyr Ser Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Ser Ser Val Tyr Ala His Tyr Tyr Gly Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

```
Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 29
<211> LENGTH: 218
<212> TYPE: PRT
<213> ORGANISM: Artificial Sequence
<220> FEATURE:
<223> OTHER INFORMATION: Humanized

<400> SEQUENCE: 29

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Val Leu Tyr Ser
            20                  25                  30

Gly Asp Asn Tyr Leu Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Asn
                85                  90                  95

Gly Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 30
<211> LENGTH: 453
<212> TYPE: PRT
<213> ORGANISM: Artificial Sequence
<220> FEATURE:
<223> OTHER INFORMATION: Humanized

<400> SEQUENCE: 30

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Gly Trp Ile Arg Gln Pro Pro Gly Lys Ala Leu Glu
```

```
                35                  40                  45
Trp Leu Ala His Ile Asp Trp Asp Asp Lys Tyr Tyr Ser Thr Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Arg Ser Ser Val Tyr Ala His Tyr Tyr Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly
                450
```

<210> SEQ ID NO 31
<211> LENGTH: 333
<212> TYPE: DNA
<213> ORGANISM: Artificial Sequence
<220> FEATURE:
<223> OTHER INFORMATION: Humanized

<400> SEQUENCE: 31

```
gatattgtga tgacccagag cccggatagc ctggcggtga gcctgggcga acgcgcgacc    60
attagctgca aagcgagcca gagcgtgctg tatagcggcg ataactatct gaactggtat   120
cagcagaaac cgggccagcc gccgaaactg ctgatttatg cggcgagcac cctggaaagc   180
ggcattccgg atcgctttag cggcagcggc agcggcaccg attttaccct gaccattagc   240
agcctgcagg cggaagatgt ggcggtgtat tattgccagc agtataacgg cgatccgtgg   300
acctttggcg gcggcaccaa agtggaaatt aaa                                333
```

<210> SEQ ID NO 32
<211> LENGTH: 372
<212> TYPE: DNA
<213> ORGANISM: Artificial Sequence
<220> FEATURE:
<223> OTHER INFORMATION: Humanized

<400> SEQUENCE: 32

```
gaagtgaccc tgcgcgaaag cggcccggcg ctggtgaaac cgacccagac cctgaccctg    60
acctgcacct ttagcggctt tagcctgagc accagcggca tgggcgtggg ctggattcgc   120
cagccgccgg gcaaagcgct ggaatggctg gcgcatattg attgggatga tgataaatat   180
tatagcccga gcctgaaaag ccgcctgacc attagcaaag ataccagcaa aaaccaggtg   240
gtgctgacca tgaccaacat ggatccggtg gataccgcga cctattattg cgcgcgcatt   300
cgcagcagcg tgtatgcgca ttattatggc atggattatt ggggccaggg caccaccgtg   360
accgtgagca gc                                                      372
```

<210> SEQ ID NO 33
<211> LENGTH: 333
<212> TYPE: DNA
<213> ORGANISM: Artificial Sequence
<220> FEATURE:
<223> OTHER INFORMATION: Humanized

<400> SEQUENCE: 33

```
gatattgtga tgacccagag cccggatagc ctggcggtga gcctgggcga acgcgcgacc    60
attagctgca aaagcagcca gagcgtgctg tatagcggcg ataactatct gaactggtat   120
cagcagaaac cgggccagcc gccgaaactg ctgatttatg cggcgagcac cctggaaagc   180
ggcattccgg atcgctttag cggcagcggc agcggcaccg attttaccct gaccattagc   240
agcctgcagg cggaagatgt ggcggtgtat tattgccagc agtataacgg cgatccgtgg   300
acctttggcg gcggcaccaa agtggaaatt aaa                                333
```

<210> SEQ ID NO 34
<211> LENGTH: 372
<212> TYPE: DNA
<213> ORGANISM: Artificial Sequence
<220> FEATURE:
<223> OTHER INFORMATION: Humanized

<400> SEQUENCE: 34

```
gaagtgaccc tgcgcgaaag cggcccggcg ctggtgaaac cgacccagac cctgaccctg    60
acctgcacct ttagcggctt tagcctgagc accagcggca tgtgcgtggg ctggattcgc   120
cagccgccgg gcaaagcgct ggaatggctg gcgcatattg attgggatga tgataaatat   180
tatagcacca gcctgaaaag ccgcctgacc attagcaaag ataccagcaa aaaccaggtg   240
gtgctgacca tgaccaacat ggatccggtg ataccgcga cctattattg cgcgcgcatt   300
cgcagcagcg tgtatgcgca ttattatggc atggatgtgt ggggccaggg caccaccgtg   360
accgtgagca gc                                                       372
```

<210> SEQ ID NO 35
<211> LENGTH: 218
<212> TYPE: PRT
<213> ORGANISM: Artificial Sequence
<220> FEATURE:
<223> OTHER INFORMATION: Humanized

<400> SEQUENCE: 35

```
Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Leu Tyr Ser
            20                  25                  30

Gly Asp Asn Tyr Leu Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Asn
                85                  90                  95

Gly Thr Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 36
<211> LENGTH: 453
<212> TYPE: PRT
<213> ORGANISM: Artificial Sequence
<220> FEATURE:
<223> OTHER INFORMATION: Humanized

<400> SEQUENCE: 36

```
Glu Val Thr Leu Arg Glu Ser Gly Pro Ala Leu Val Lys Pro Thr Gln
1               5                   10                  15
```

-continued

```
Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Ala Leu Glu
         35                  40                  45

Trp Leu Ala His Ile Asp Trp Asp Asp Lys Tyr Tyr Ser Thr Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Arg Ser Ser Val Tyr Ala His Tyr Tyr Gly Met Asp
             100                 105                 110

Tyr Trp Gly Gln Gly Thr Thr Val Thr Val Ser Ser Ala Ser Thr Lys
         115                 120                 125

Gly Pro Ser Val Phe Pro Leu Ala Pro Ser Ser Lys Ser Thr Ser Gly
     130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                 165                 170                 175

Phe Pro Ala Val Leu Gln Ser Ser Gly Leu Tyr Ser Leu Ser Ser Val
             180                 185                 190

Val Thr Val Pro Ser Ser Ser Leu Gly Thr Gln Thr Tyr Ile Cys Asn
         195                 200                 205

Val Asn His Lys Pro Ser Asn Thr Lys Val Asp Lys Lys Val Glu Pro
     210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                 245                 250                 255

Thr Leu Met Ile Ser Arg Thr Pro Glu Val Thr Cys Val Val Val Asp
             260                 265                 270

Val Ser His Glu Asp Pro Glu Val Lys Phe Asn Trp Tyr Val Asp Gly
         275                 280                 285

Val Glu Val His Asn Ala Lys Thr Lys Pro Arg Glu Glu Gln Tyr Asn
     290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                 325                 330                 335

Ala Pro Ile Glu Lys Thr Ile Ser Lys Ala Lys Gly Gln Pro Arg Glu
             340                 345                 350

Pro Gln Val Tyr Thr Leu Pro Pro Ser Arg Asp Glu Leu Thr Lys Asn
         355                 360                 365

Gln Val Ser Leu Thr Cys Leu Val Lys Gly Phe Tyr Pro Ser Asp Ile
     370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                 405                 410                 415

Leu Thr Val Asp Lys Ser Arg Trp Gln Gln Gly Asn Val Phe Ser Cys
             420                 425                 430

Ser Val Met His Glu Ala Leu His Asn His Tyr Thr Gln Lys Ser Leu
```

```
                435                 440                 445
Ser Leu Ser Pro Gly
        450

<210> SEQ ID NO 37
<211> LENGTH: 218
<212> TYPE: PRT
<213> ORGANISM: Artificial Sequence
<220> FEATURE:
<223> OTHER INFORMATION: Humanized

<400> SEQUENCE: 37

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Val Leu Tyr Ser
            20                  25                  30

Ser Asn Asn Tyr Leu Asn Trp Tyr Gln Gln Lys Pro Gly Gln Pro Pro
        35                  40                  45

Lys Leu Leu Ile Tyr Ala Ala Ser Thr Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Ser Thr Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 38
<211> LENGTH: 453
<212> TYPE: PRT
<213> ORGANISM: Artificial Sequence
<220> FEATURE:
<223> OTHER INFORMATION: Humanized

<400> SEQUENCE: 38

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Asp Trp Asp Asp Asp Lys Tyr Tyr Ser Thr Ser
    50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Arg Ser Ser Val Tyr Tyr Tyr Tyr Gly Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
450
```